US005925656A

United States Patent [19]
Kallam et al.

[11] Patent Number: 5,925,656
[45] Date of Patent: Jul. 20, 1999

[54] COMPOUNDS HAVING ANTIDIABETIC, HYPOLIPIDEMIC, ANTIHYPERTENSIVE PROPERTIES, PROCESS FOR THEIR PREPARATION AND PHARMACEUTICAL COMPOSITIONS CONTAINING THEM

[75] Inventors: Anji Reddy Kallam; Vidya Bhushan Lohray; Sekhar Reddy Alla; Harikishore Pingali; Rajagopalan Ramanujam, all of Hyderabad; Seshagiri Rao Casturi, Secunderabad, all of India

[73] Assignee: Dr. Reddy's Research Foundation, Hyderabad, India

[21] Appl. No.: 08/621,226

[22] Filed: Mar. 25, 1996

Related U.S. Application Data

[63] Continuation-in-part of application No. 08/476,385, Jun. 7, 1995.

[30] Foreign Application Priority Data

Apr. 10, 1995 [IN] India ............................... 43/MAS/95

[51] Int. Cl.⁶ ..................... C07D 417/12; A61K 31/425
[52] U.S. Cl. .......................... 514/369; 546/280; 548/183
[58] Field of Search ........................... 548/183; 546/280; 514/369

[56] References Cited

U.S. PATENT DOCUMENTS

| | | | |
|---|---|---|---|
| 4,342,771 | 8/1982 | Schnur | 424/263 |
| 4,367,234 | 1/1983 | Schnur | 424/272 |
| 4,725,610 | 2/1988 | Meguro | 514/369 |
| 4,873,255 | 10/1989 | Yoshioka | 514/369 |
| 5,002,953 | 3/1991 | Hindley | 514/275 |
| 5,036,079 | 7/1991 | Clark | 514/333 |
| 5,037,842 | 8/1991 | Goldstein | 514/375 |
| 5,130,379 | 7/1992 | Clark | 514/333 |
| 5,153,210 | 10/1992 | Ainsworth | 514/369 |
| 5,296,605 | 3/1994 | De Nanteuil . | |
| 5,330,999 | 7/1994 | De Nanteuil . | |
| 5,420,146 | 5/1995 | Malamas | 514/364 |
| 5,468,762 | 11/1995 | Malamas | 514/376 |
| 5,478,851 | 12/1995 | Cantello | 514/369 |
| 5,478,852 | 12/1995 | Olefsky | 514/369 |
| 5,478,853 | 12/1995 | Regnier | 514/369 |
| 5,480,896 | 1/1996 | Malamas | 514/364 |
| 5,498,621 | 3/1996 | Dow | 514/369 |
| 5,521,201 | 5/1996 | Hindley | 514/369 |
| 5,578,620 | 11/1996 | Fujita | 514/370 |

FOREIGN PATENT DOCUMENTS

| | | |
|---|---|---|
| 008203 | 2/1980 | European Pat. Off. . |
| 155845 | 9/1985 | European Pat. Off. . |
| 0332332 | 9/1989 | European Pat. Off. . |
| 590973 | 4/1994 | European Pat. Off. . |
| 605228 | 7/1994 | European Pat. Off. . |
| 645387 | 3/1995 | European Pat. Off. . |
| 0676398 | 10/1995 | European Pat. Off. . |
| 0678511 | 10/1995 | European Pat. Off. . |
| 745600 | 12/1996 | European Pat. Off. . |
| 64-52752 | 2/1989 | Japan . |
| 2558473 | 11/1996 | Japan . |
| 9112003 | 8/1991 | WIPO . |
| 9207838 | 5/1992 | WIPO . |
| 9207850 | 5/1992 | WIPO . |
| 9425026 | 11/1994 | WIPO . |
| 9507697 | 3/1995 | WIPO . |
| 9535108 | 12/1995 | WIPO . |

OTHER PUBLICATIONS

D.A. Clark et al. "Substituted Dihydrobenzopyran . . . " J. Med. Chem. 1991, 34, 319–325.
R.L. Dow et al. "Benzyloxzolidine–2,4–diones . . . " J. Med. Chem. 1991, 34, 1538–1544.
Behavioural Brain Research 75 (1996) p. 1–1.1.
T. Sohda et al. "Studies on Antidiabetic . . . " J. Med. Chem, 1992, vol. 35. No. 14, 2617–2626.
B. Hulin et al. "Novel Thiazolidine . . . " J. Med. Chem, 1992, vol. 35, No. 10, 1853–1861.
S.W. Goldstein et al. Hydroxyurea Derivatives, J. Med. Chem, 1993, 36, 2238–2240.
Journal of Medicinal Chemistry vol. 37, No. 23, 1994 Barrie, CC. et al. pp. 3977–3985.
Chemical and Pharmaceutical Bulletin vol. 30, No. 10, 1982 pp. 3580–3600, Takashi Sohda et al.
G. De Nanteuil, "Euglygaemic and Biological Activities of Novel Thiazolidine–2,4–dione Derivatives" Arzneittel Forschung/Drug Design, vol. 45, No. II, 1995, pp. 1176–1181.
Whitcomb, R.W., "Thiazolidinediones", Expert Opinion on Investigational Drugs, vol. 4, No. 12, Dec. 1995, pp. 1299–1309.
Khan. A., et al., "Synthesis and Antibacterial Activity of Some New 2–aryloxymethyl–3–substituted–quinazollin–4 (3H)–ones" Pharmazie vol. 43, No. 12, pp. 864–865, 1988.
Chemical Abstracts, vol. 93, No. 17, Oct. 27, 1980, No. 168217.
Shukla, J.S. et al. "Synthesis of 2–phenoxymethyl–3(2'–pyridyl/thiazolyl)–4–quinazolones as Possible Antifertility Drugs" Indian Journal Chemical, vol. 17B, No. 6, pp. 651–652, Jun. 1979.
Husain, M.I., et al., "Some New 2–aryloxymethyl–3–.alpha.–substituted carboxymethyl–6,8 substituted 4–quinazolones as Possible Anticonvulsants", Pharmazie, vol. 37, No. 6, 1982, pp. 408–410.

*Primary Examiner*—Robert Gerstl
*Attorney, Agent, or Firm*—Ladas & Parry

[57] ABSTRACT

Thiazolidinediones of formula (I) their tautomeric forms, their derivatives, their stereoisomers, their polymorphs, their pharmaceutically acceptable salts, their pharmaceutically acceptable solvates and pharmaceutical compositions containing them having antidiabetic, hypolipidemic, and antihypertensive properties have been prepared.

$$A-B-\overset{R}{\underset{|}{N}}-D-X-Ar-\overset{R^1}{\underset{|}{C}}H-\overset{R^2}{\underset{|}{C}}\begin{array}{c}O\\ \diagdown\\ NH\\ \diagup\\ S\diagdown\\ \phantom{S}\diagup\\ O\end{array} \quad (I)$$

49 Claims, No Drawings

COMPOUNDS HAVING ANTIDIABETIC, HYPOLIPIDEMIC, ANTIHYPERTENSIVE PROPERTIES, PROCESS FOR THEIR PREPARATION AND PHARMACEUTICAL COMPOSITIONS CONTAINING THEM

This application is a continuation-in-part of application Ser. No. 08/476,385 filed on Jun. 7, 1995, allowed.

FIELD OF THE INVENTION

The present invention relates to novel antidiabetic compounds, their tautomeric forms, their derivatives, their pharmaceutically acceptable salts, their pharmaceutically acceptable solvates and pharmaceutically acceptable compositions containing them. This invention particularly relates to novel thiazolidinedione derivatives (I), and their pharmaceutically acceptable salts, pharmaceutically acceptable solvates and a pharmaceutical composition containing them.

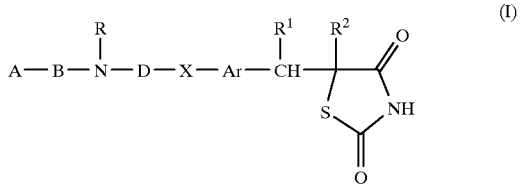

The present invention also relates to a process for the preparation of the above said novel, thiazolidinedione derivatives, their tautomeric forms, their pharmaceutically acceptable salts, pharmaceutically acceptable solvates, novel intermediates and pharmaceutical compositions containing them.

The present invention relates to novel antidiabetic compounds, their tautomeric forms, their derivatives, their pharmaceutically acceptable salts, their pharmaceutically acceptable solvates and pharmaceutical compositions containing them. This invention particularly relates to novel thiazolidinedione derivatives of the formula (I), their tautomeric forms, their derivatives, their pharmaceutically acceptable salts and pharmaceutically acceptable compositions containing them.

The thiazolidinedione derivatives of the present invention are useful for the treatment of diseases such as type II diabetes, hyperlipidaemia, hypertension, other cardiovascular disorders including atherosclerosis as well as certain eating disorders.

The present invention also relates to a process for the preparation of the above said novel thiazolidinedione derivatives, their tautomeric forms, their pharmaceutically acceptable salts, their pharmaceutically acceptable solvates and novel intermediates.

BACKGROUND OF THE INVENTION

The most significant and effective drug for the treatment of diabetes after the advent of the sulfonyl ureas has been the development of a group of compounds by Takeda, which are the derivatives of 5-(4-alkoxybenzyl)-2,4-thiazolidinediones of the formula (II) (Ref. Chem. Pharm. Bull. 1982, 30, 3580–3600). In the formula (II), V represents substituted or unsubstituted divalent aromatic group and U represents various groups which have been reported in various patent documents.

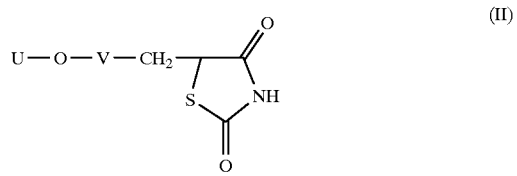

By way of examples, U may represent the following groups:

(i) a group of the formula (IIa) where $R^1$ is hydrogen or hydrocarbon residue or heterocyclic residue which may each be substituted, $R^2$ is hydrogen or a lower alkyl which may be substituted by hydroxy group, X is an oxygen or sulphur atom, Z is a hydroxylated methylene or a carbonyl, m is 0 or 1, n is an integer of 1–3. These compounds have been disclosed in the European Patent Application No. 0 177 353

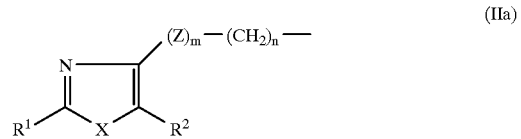

An example of these compounds is shown in formula (IIb)

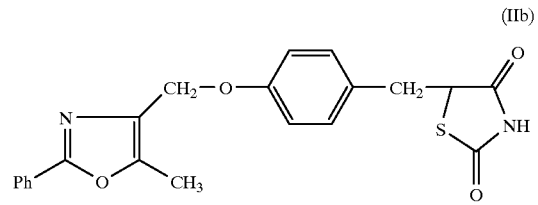

(ii) a group of the formula (IIc) wherein $R^1$ and $R^2$ are the same or different and each represents hydrogen or $C_1$–$C_5$ alkyl, $R^3$ represents hydrogen, acyl group, a ($C_1$–$C_6$) alkoxycarbonyl group or aralkyloxycarbonyl group, $R^4$–$R^5$ are same or different and each represent hydrogen, $C_1$–$C_5$ alkyl or $C_1$–$C_5$ alkoxy or $R^4$, $R^5$ together represent $C_1$–$C_4$ alkenedioxy group, n is 1, 2, or 3, W represents $CH_2$, CO, CHOR$^6$ group in which $R^6$ represents any one of the items or groups defined for $R^3$ and may be the same or different from $R^3$. These compounds are disclosed in the European Patent Application No. 0 139 421.

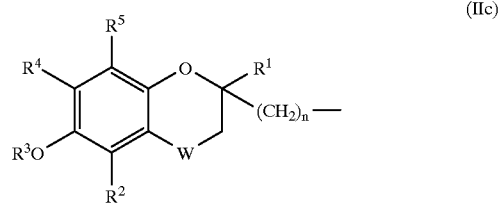

An example of these compounds is shown in (IId)

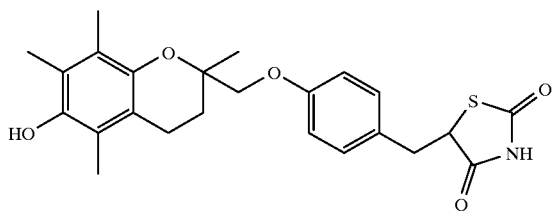

iii) A group of formula (IIe) where $A^1$ represents substituted or unsubstituted aromatic heterocyclic group, $R^1$ represents a hydrogen atom, alkyl group, acyl group, an aralkyl group wherein the aryl moiety may be substituted or unsubstituted, or a substituted or unsubstituted aryl group, n represents an integer in the range from 2 to 6. These compounds are disclosed in European Patent No. 0 306 228.

An example of this compound is shown in formula (IIf)

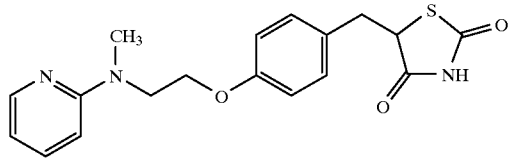

iv) A group of formula (IIg) where Y represents N or $CR^5$, $R^1$, $R^2$, $R^3$, $R^4$ and $R^5$ represents hydrogen, halogen, alkyl and the like and $R^6$ represents hydrogen, alkyl, aryl and the like, n represents an integer of 0 to 3. These compounds are disclosed in European Patent Application 0 604 983.

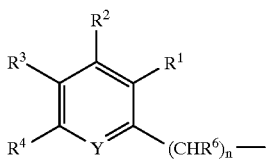

An example of this compound is shown in formula (IIh)

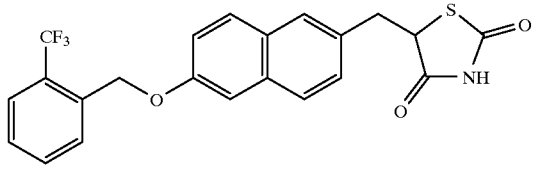

Some of the above referred hitherto known antidiabetic compounds seem to possess bone marrow depression, liver and cardiovascular toxicities and modest potency and consequently their regular use for the treatment and control of diabetes is becoming limited and restricted.

SUMMARY OF THE INVENTION

With an object of developing newer compounds for the treatment of type II diabetes [non-insulin-dependent-diabetes mellitus (NIDDM)] which could be more potent at relatively lower doses and better efficacy having lower toxicity, we focussed our research efforts in a direction of incorporating safety factor and to have better efficacy, which has resulted in the development of novel thiazolidinedione derivatives having the general formula (I) as defined above.

The main objective of the present invention is therefore, to provide novel thiazolidinedione derivatives, their tautomeric forms, their pharmaceutically acceptable salts, their pharmaceutically acceptable solvates and pharmaceutical compositions containing them, or their mixtures.

Another objective of the present invention is to provide novel thiazolidinedione derivatives, their tautomeric forms, their pharmaceutically acceptable salts, their pharmaceutically acceptable solvates and pharmaceutical compositions containing them or their mixtures having enhanced activities, no toxic effect or reduced toxic effect.

DETAILED DESCRIPTION OF THE INVENTION

Thiazolidinedione derivatives of the present invention have the general formula (I)

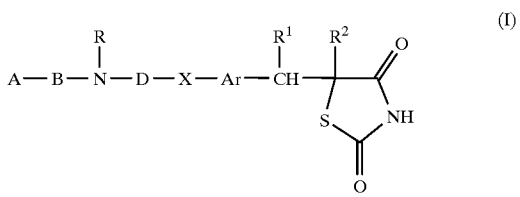

In the formula (I), A represents substituted or unsubstituted unsaturated aliphatic, alicyclic, aromatic, heterocyclic groups, B represents substituted or unsubstituted divalent alkylene or alkenyl group, having 1 to 10 carbon atoms, the substituents may be present in one or more of the divalent alkylene or alkenyl group, D represents a substituted or unsubstituted divalent alkylene or alkenyl group, R represents a hydrogen atom, substituted or unsubstituted alkylene alkynyl alkenyl or alkynyl group, aralkyl group, alkoxycarbonyl or aryloxycarbonyl groups, X represents $CH_2$, $C=O$, $CH-OH$, sulphur, oxygen atoms, N-Y, where Y represents hydrogen atom, substituted or unsubstituted alkyl, aryl, aralkyl or an acyl group. Ar represents a divalent aromatic, single or fused ring system, with or without substituents, the ring may contain one or more hetero atoms selected from nitrogen, sulphur, oxygen atoms. $R^1$ and $R^2$ each represents hydrogen atoms or together represent a bond, either or both may be substituents or both together form a part of a ring.

Suitable aliphatic groups that may form the A group include alkenyl and alkynyl groups of 1 to 10 carbon atoms, typically of from 1 to 5 carbon atoms. A may also be a cycloalkyl or cycloalkenyl group of 3 to 10 carbon atoms either as a single or as a fused ring system.

Suitable aromatic groups include phenyl, naphthyl, phenanthryl groups and their partially hydrogenated derivatives such as tetrahydronaphthyl group.

Heterocyclic groups may have one or more five or six membered rings and may contain up to five hetero atoms selected from oxygen, sulfur and nitrogen. These groups may also be aromatic or may be partially hydrogenated like dihydrobenzofuranyl group.

The A groups may be substituted or unsubstituted and suitable substituents include alkyl of 1 to 10 carbon atoms, alkoxy of 1 to 10 carbon atoms, aryl of single or fused, five or six membered rings, halo (particularly fluoro, chloro or bromo), aralkyl such as benzyl and phenethyl, aryloxy such as phenyloxy, naphthyloxy, aralkoxy (for example, benzyloxy, phenethyloxy), amino, mono or dialkylamino where each alkyl group is of from 1 to 8 carbon atoms, carboxy group, formyl group, alkylcarbonyl of 2 to 10 carbon atoms, arylcarbonyl, such as benzoyl and naphthoyl, aryloxycarbonyl, arylcarbonyloxy such as benzoate, alkylcarbonyloxy such as acetate, propionate, butyrate and hexanoate groups, hydroxy, thio, thioalkyl, hydroxyalkyl, haloalkyl, aminoalkyl, nitro and cyano groups. Particularly useful A groups include: 6-benzyloxy-2,5,7,8-tetramethylchroman-2-yl, 6-hydroxy-2,5,7,8-tetramethylchroman-2-yl, 2-pyridyl, 5-methyl-2-phenyl-4-oxazolyl, 2,3-dihydro-5-hydroxy 2,2,4,6,7-pentamethyl-1-benzofuran-3-yl, 2-benzothiazolyl groups.

B groups may have from 1 to 10 carbon atoms, preferably from 1 to 4 carbon atoms. Suitable substituents on B include lower alkylene, alkoxy of 2 to 6 carbon atoms, aralkoxy, amino, alkylamino, dialkylamino, hydroxyalkyl, aminoalkyl, thio, thioalkyl, halo, haloalkyl, carboxy, alkoxycarbonyl, aryloxycarbonyl, alkylcarbonyloxy, arylcarbonyloxy groups. Particularly useful B groups include methylene, ethylene, alkylmethylene, alkylethylene, hydroxyalkyl methylene or ethylene, aminoalkylene.

Suitable R groups could be hydrogen, substituted or unsubstituted alkyl, alkenyl or alkynyl groups of from 1 to 10 carbon atoms, preferably of from 1 to 6 carbon atoms, aralkyl groups such as benzyl, phenethyl and naphthylmethyl groups. R groups may also be alkoxycarbonyl or aryloxycarbonyl groups when A groups are not aryl groups such as phenyl or naphthyl. The aryl moiety of an aralkyl group may be substituted by any substituents that may be selected from the same groups that may substitute A.

D groups may have from 1 to 10 carbon atoms, preferably from 1 to 4 carbon atoms. Suitable substituents include hydroxy and any substituent that may substitute B.

Y groups of N-Y comprising the X moiety are typically hydrogen, alkylene, alkenyl or alkynyl groups of from 1 to 10 carbon atoms, preferably of from 1 to 6 carbon atoms, aryl groups such as phenyl and naphthyl, aralkyl such as benzyl and phenethyl. Such groups may, if desired be substituted by groups such as alkyl, alkoxy, hydroxy, halo and amino groups. Alternatively, Y may be an acyl group of 2 to 14 carbon atoms, for example, an alkanoyl group of 2 to 8 carbon atoms or an optionally substituted benzoyl group, wherein any substituent is selected from the same group, that may substitute R.

Suitable Ar groups include phenyl, naphthyl, pyridyl, furyl, benzofuryl, benzopyranyl, benzoxazolyl and benzothiazolyl groups. Such groups may be substituted by any of the same groups that may substitute A as mentioned above.

$R^1$ and $R^2$ represent hydrogen or jointly form a bond resulting in an unsaturated link between the thiazolidinedione ring and the adjacent carbon atom. Alternatively, $R^1$ and $R^2$ jointly form a part of a ring of 5 to 7 carbon atoms, together with carbon atoms bearing $R^1$ and $R^2$. $R^1$ and $R^2$ may either or both be substituents that may be selected from the same group that may substitute D.

Pharmaceutically acceptable salts forming part of this invention include salts of the thiazolidinedione moiety such as alkali metal salts like Li, Na, & K salts and salts of carboxy group wherever appropriate, such as aluminum, alkali metal salts, alkaline earth metal salts, ammonium or substituted ammonium salts. Salts may include acid addition salts which are sulphates, nitrates, borates, hydrohalides, acetates, tartrates, maleates, citrates, succinates, methanesulphonates, benzoates, ascorbates, glycerophosphates, ketoglutarates and the like. Pharmaceutically acceptable solvate may be hydrates.

Particularly useful compounds according to the invention include: 5-[4-[2-[N-(6-benzyloxy-2,5,7,8-tetramethylchroman-2-ylmethyl)-N-methylamino]ethoxy] benzyl]thiazolidine-2,4-dione, 5-[4-[2-[N-(6-hydroxy-2,5,7, 8-tetramethylchroman-2-ylmethyl)-N-methylamino]ethoxy] benzyl]thiazolidine-2,4-dione, 5-[4-[2-[N-(6-benzyloxy-2, 5,7,8-tetramethylchroman-2-ylmethyl)-N-methylamino] ethoxy]phenyl methylene]thiazolidine-2,4-dione, 5-[4-[2-[N-(6-hydroxy-2,5,7,8-tetramethylchroman-2-ylmethyl)-N-methylamino]ethoxy]phenyl methylene]thiazolidine-2,4-dione, 5-[4-[2-[N-[2-(6-hydroxy-2,5,7,8-tetramethylchroman-2-yl)ethyl]-N-methylamino]ethoxy] benzyl]thiazolidine-2,4-dione, 5-[4-[2-[N-methyl-N-(2-pyridyl methyl)amino]ethoxy]benzyl]thiazolidine-2,4-dione, 5-[4-[2-[N-methyl-N-(2-pyridyl methyl)amino] ethoxy]phenyl methylene]thiazolidine-2,4-dione, 5-[4-[2-[N-methyl-N-(5-methyl-2-phenyl-4-oxazolyl)methylamino] ethoxy]benzyl]thiazolidine-2,4-dione, 5-[4-[2-[N-methyl-N-(5-methyl-2-phenyl-4-oxazolyl)methylamino]ethoxy] phenyl methylene]thiazolidine-2,4-dione, 5-[4-[2-[N-(2,3-dihydro-5-hydroxy-2,2,4,6,7-pentamethyl-1-benzofuran-3-ylmethyl)-N-methylamino]ethoxy]phenyl methylene] thiazolidine-2,4-dione, 5-[4-[2-[N-(2,3-dihydro-5-hydroxy-2,2,4,6,7-pentamethyl-1-benzofuran-3-ylmethyl)-N-methylamino]ethoxy]benzyl]thiazolidine-2,4-dione.

Another objective of the present invention is to provide novel intermediates which also possess similar activity as of the thiazolidinedione derivatives of the general formula (I) as defined above.

The novel intermediates have the general formula (III) and (IV)

(III)

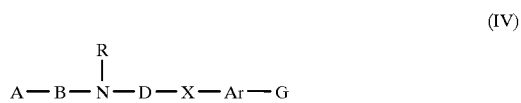

(IV)

wherein, A, B, R, D, X, Ar are as defined earlier, E represents hydroxy, halogen (Cl, Br, I), methanesulphonates, p-toluenesulphonates, trifluoromethanesulphonates, etc. and G represents CHO, $NO_2$, $NH_2$, $CH_2$—$CHR^a$—$COOR^b$ wherein $R^a$ is halogen atom and $R^b$ represents hydrogen, alkyl, aralkyl group etc.

Still another objective of the present invention is to produce a process for the preparation of thiazolidinedione derivatives of the formula (I) as defined above.

Yet another objective of the present invention is to provide a pharmaceutical composition containing the compound of the formula (I), their tautomers, their salts, solvates or their mixtures in combination with suitable carriers, diluents and media normally employed in preparing such composition.

Accordingly, the present invention provides a process for the preparation of novel thiazolidinedione derivatives, their tautomeric forms, their pharmaceutically acceptable salts, their pharmaceutically acceptable solvates of the formula (I) wherein each of the symbol is as defined earlier, which comprises (a) reacting a compound of the general formula (V)

 (V)

where A, B are as defined earlier, $L^1$ is a leaving group such as OMs, OTf, OTs, Cl, Br, I, with the compound of general formula (VI)

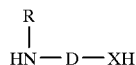 (VI)

where D and R are as defined earlier, X may be oxygen, sulphur or NH to yield a compound of the general formula (VII)

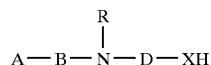 (VII)

where A, B, R, D, X are as defined earlier.

b) reacting a compound of general formula (VII) obtained in step (a) with a compound of general formula (VIII)

 (VIII)

where $L^2$ represents a halogen atom and Ar is as defined earlier, in an inert atmosphere to yield a compound of general formula (IX)

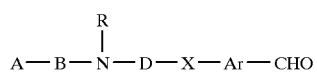 (IX)

where A, B, R, D, Ar are as defined earlier, X may be oxygen, sulfur or other hetero atoms.

(c) reacting the compound of the general formula (IX) obtained in step (b) with 2,4-thiazolidinedione to yield a compound of general formula (X).

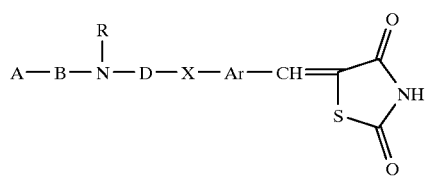 (X)

where A, B, R, D, Ar, X are as defined earlier and removing the water formed during the reaction by conventional methods.

(d) reducing by known method the compound of the general formula (X) obtained in step (c) to obtain the compound of general formula (I) as defined above and if desired, (e) converting the compound of the general formula (I) obtained in step (d) into their pharmaceutically acceptable salts, their pharmaceutically acceptable solvates by conventional methods.

In an embodiment of the invention, the novel intermediate of the general formula (IX) defined and obtained in the step (b) above can be prepared by reacting the compound of the general formula (XI) wherein A, B, R, D, $L^1$ as defined earlier which compound of the general formula (XII) where Ar is as defined earlier

 (XI)

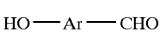 (XII)

The compound of general formula (XI) used for the preparation of the compound of the general formula (IX) can be prepared by reacting a compound of general formula (VII) with $MeSO_2Cl$, p-TsCl, $CBr_4/PPh_3$, $CCl_4/PPh_3$, $CI_4/PPh_3$, $SOCl_2$ or such other halogenating agents.

In another embodiment of the present invention, the compound of the general formula (I), their tautomeric forms, their pharmaceutically acceptable salts and their pharmaceutically acceptable solvates can also be prepared by reacting a compound of the general formula (XI) where A, B, R, D, $L^1$ are as defined above with a compound of the general formula (XIII)

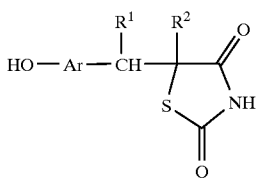 (XIII)

wherein, Ar, $R^1$, $R^2$ are as defined above.

In yet another embodiment of the invention, the compound of the general formula (I) as defined above can also be prepared by reacting a compound of the general formula (VII) with a substituted halonitroarene of the general formula (XIV), to produce a novel intermediate compound of the general formula (XV) where $L^2$ represents halogen atom and each of the symbol is as defined earlier and reducing by known methods the compound of the general formula (XV) to yield a compound of general formula (XVI),

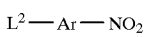 (XIV)

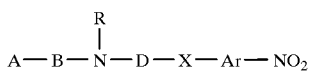 (XV)

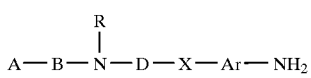 (XVI)

wherein A, B, R, D, Ar, X are as defined before, diazotizing the compound of general formula (XVI) by known methods, followed by treatment with acrylic acid or its esters to yield a compound of general formula (XVII)

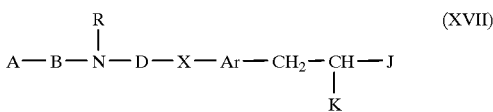

wherein each of the symbol is as defined earlier, K is a halogen atom and J is an acid or an ester group and treating the resulting compound of the general formula (XVII) with thiourea followed by hydrolysis by known methods to yield the compound of general formula (I) as defined before.

In another embodiment of the invention, the intermediate of the general formula (XV) defined and obtained as above, can be prepared by reacting the compound of the general formula (XI)

where A, B, R, D and $L^1$ are as defined earlier, with a compound of formula (XVIII)

where X and Ar are as defined earlier.

The amount of compound of the formula (V) and the compound of the formula (VI) used in the step (a) may range from 1 to 2 equivalents and from 1 to 200 equivalents, respectively. The temperature employed may range from 20° C.–200° C., preferably ranging from 50° C.–150° C. The reaction time normally may range from 2–70 hours, preferably it may range from 6 to 48 hours.

The reaction of the compound of formula (VII) with compound of the formula (VIII) in step (b) to produce a compound of the formula (IX) may be carried out in the presence of solvents such as THF, DME, DMSO, DME. The inert atmosphere is maintained by using inert gases such as $N_2$, Ar, He. The reaction may be effected in the presence of a base such as $K_2CO_3$, $Na_2CO_3$, NaH. The reaction temperature may range from 20° C.–120° C., preferably, at a temperature in the range of 30° C.–80° C. The duration of the reaction may range from 1–12 hours, preferably from 2 to 6 hours.

The reaction between the compound of the general formula (IX) with 2,4-thiazolidinedione in step (c) may be carried out neat or in the presence of a solvent such as benzene, toluene, methoxyethanol. The reaction temperature may range from 80 to 140° C. depending upon the solvents employed. Suitable catalyst such as piperidinium acetate or benzoate, sodium acetate may also be employed. The water produced in the reaction may be removed, for example, by using Dean Stark water separator or by using water absorbing agents like molecular seives.

The reduction of the compound of the formula (X) in step (d) to yield a compound of the general formula (I) may be carried out in the presence of gaseous hydrogen and a catalyst such as Pd/C, Rh/C, Pt/C, and the like. The reaction may also be conducted in the presence of solvents such as dioxane, acetic acid, ethyl acetate and the like. A pressure between atmospheric pressure and 80 psi may be employed. The catalyst may be 5–10% Pd/C and the amount of catalyst used may range from 50–100% w/w. The reaction may also be carried out by employing metal solvent reduction such as magnesium in methanol or sodium amalgam in methanol.

The reaction between the compound of the formula (XI) and the compound of the formula (XII) may be carried out in the presence of solvents such as DMF, DMSO, THF. The reaction may be effected in the presence of a base such as sodium hydride or potassium carbonate. The temperature may range from 20° C.–120° C., preferably at 30° C.–80° C. The reaction may be conducted for a period ranging from 2–12 hours, preferably from 4 to 12 hours.

The reaction of compound of formula (XI) with compound of general formula (XIII) may be carried out in the presence of solvents such as DMF, DMSO, THF. The reaction may also be effected in the presence of a base such as sodium hydride or potassium carbonate. The temperature of the reaction may range from 0–120° C., preferably from 20 to 100° C. The duration of the reaction may range from 1–24 hours, preferably from 2 to 8 hours.

The reaction of compound of general formula (VII) with halosubstituted nitroarenes of formula (XIV) may be carried out in the presence of polar solvents such as DMF, DMSO, THF. The reaction may also be effected in the presence of a base such as sodium hydride or potassium carbonate. The temperature of the reaction may range from 0–120° C., preferably from 20 to 80° C. The duration of reaction may range from 2–12 hours, preferably from 2 to 8 hours.

The subsequent reaction of the compound of the general formula (XV) to prepare the compound of the general formula (XVI) may be carried out by reduction. The reagents such as $H_2$/Pd/C or zinc or iron and acetic acid, tin and hydrochloric acid, metal hydrides such as lithium aluminum hydride and the like may be used.

The diazotization of the compound of the formula (XVI) may be carried out with alkali metal nitrites and the resulting diazo compound is treated with acrylic acid or its esters in the presence of copper oxide as a catalyst in the presence of hydrohalo acid to give a compound of formula (XVII).

The reaction of the compound of the general formula (XVII) with thiourea is normally carried out in the presence of protic solvents such as methanol, ethanol, propanol, isopropanol, butanol, isobutanol, 2-methoxybutanol etc. or DMSO or sulfolane. The reaction may be conducted at a temperature in the range between 20–180° C. preferably in the range of 20 to 100° C. The reaction may also be conducted in the presence of alkali metal acetate like NaOAc, KOAc etc. followed by hydrolysis. The hydrolysis may be carried out by using aqueous or alcoholic mineral acids such as hydrohalo acids, sulfuric acid etc. at 50–100° C.

The reaction of compound of formula (XI) with compound of formula (XVIII) is carried out in the presence of polar solvents such as DMF, DMSO, THF in the presence of a base such as sodium hydride or potassium carbonate under inert atmosphere of nitrogen, argon or the like. The temperature of the reaction may range between 20–120° C., preferably at 30–100° C. The reaction may be conducted for a period ranging from 1–24 hours, preferably from 2–6 hours.

The pharmaceutically acceptable salts are prepared by reacting the compound of formula (I) with one equivalent of a base such as sodium hydroxide, sodium methoxide, sodium hydride in solvents like ether, THF etc. Alternatively, they are prepared by treatment with acids such as hydrochloric acid, hydrobromic acid, p-toluene sulphonic acid, methane sulfonic acid, acetic acid, citric acid, maleic acid and the like in solvents like ethyl acetate, ether, alcohols etc.

The present invention also provides a pharmaceutical composition, containing the compounds of the general formula (I), as defined above, their tautomeric forms, their pharmaceutically acceptable salts, their pharmaceutically acceptable solvates in combination with the usual pharmaceutically employed carriers, diluents and the like, useful for the treatment of type II diabetes, as a hypoglycemic agent, for prophylactic treatment, hyperlipidaemia, hypertension, other cardiovascular diseases including atherosclerosis as well as certain eating disorders. The pharmaceutical composition may be in the forms normally employed, such as tablets, capsules, powders, syrups, solutions, suspensions and the like, may contain flavourant, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carrier, diluent or solvent.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day or preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in amounts sufficient to provide the desired dosage amount in the range described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts of the compounds. The injectable solutions prepared in this manner can then be administered intravenously, intraperitoneally, subcutaneously, or intramuscularly, with intramuscular administration being preferred in man.

The invention is described in detail in the examples given below which are provided by way of illustration only and therefore should not be construed to limit the scope of the invention.

Preparation 1

2-[N-(6-Benzyloxy-2,5,7,8-tetramethylchroman-2-ylmethyl)-N-methylamino]ethanol

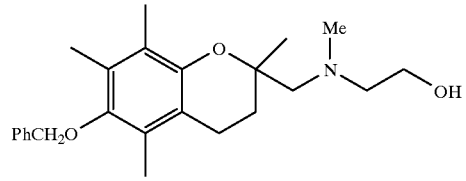

A mixture of 6-benzyloxy-2,5,7,8-tetramethylchroman-2-ylmethyl methanesulphonate (20 g) and 2-(methylamino)ethanol (80 ml) was heated under nitrogen atmosphere at 120° C. with stirring for 12 h. The mixture was cooled to room temperature and poured into water and the solution was extracted with ethyl acetate repeatedly. The combined organic extracts were washed with brine, dried ($Na_2SO_4$) and evaporated to dryness under reduced pressure to give 18 g of the title compound.

$^1$H NMR ($CDCl_3$, 200 MHz): δ1.2 (s, 3H), 1.7 (m, 1H), 2.0 (m, 1H), 2.15 (s, 3H), 2.2 (s, 3H), 2.25 (s, 3H), 2.45 (s, 3H), 2.55–2.85 (m, 6H), 3.6 (t, J=5.1 Hz, 2H), 4.7 (s, 2H), 7.3–7.55 (m, 5H).

Preparation 2

2-[N-[2-(6-Benzyloxy-2,5,7,8-tetramethylchroman-2-yl)ethyl]-N-methylamino]ethanol

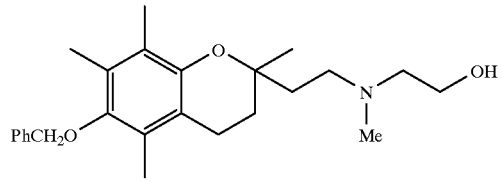

The title compound was prepared from 6-benzyloxy-2,5,7,8-tetramethylchroman-2-ylethyl methanesulphonate (3.8 g) and 2-(methylamino)ethanol (7.2 ml) by an analogous procedure to that described in preparation 1.

$^1$H NMR ($CDCl_3$, 200 MHz): δ1.25 (s, 3H), 1.8 (m, 4H), 2.1 (s, 3H), 2.15 (s, 3H), 2.23 (s, 3H), 2.25 (s, 3H), 2.5–2.7 (m, 6H), 3.55 (t, J=6.4 Hz, 2H), 4.7 (s, 2H), 7.3–7.55 (m, 5H).

Preparation 3

2-[N-(6-Benzyloxy-2,5,7,8-tetramethylchroman-2-ylmethyl)amino]ethanol

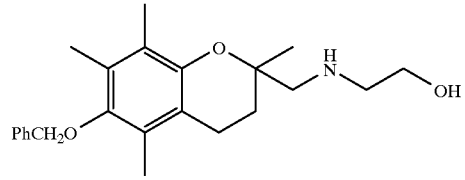

The title compound was prepared from 6-benzyloxy-2,5,7,8-tetramethylchroman-2-ylmethyl methanesulphonate (4 g) and ethanol amine (12 ml) by an analogous procedure to that described in preparation 1.

¹H NMR (CDCl₃, 200 MHz): δ1.30 (s, 3H), 1.65–1.83 (m, 1H), 1.95–2.06 (m, 1H), 2.11 (s, 3H), 2.19 (s, 3H), 2.24 (s, 3H), 2.65 (t, J=7.2 Hz, 2H), 2.79 (s, 2H), 2.85 (m, 2H), 3.63 (t, J=5.2 Hz, 2H), 4.71 (s, 2H), 7.35–7.63 (m, 5H).

Preparation 4

2-[N-(6-Benzyloxy-2,5,7,8-tetramethylchroman-2-ylmethyl)-N -ethylamino]ethanol

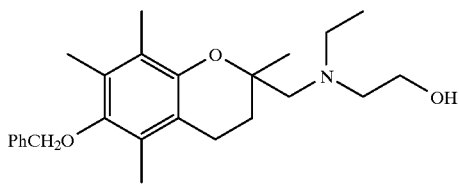

The title compound was prepared from 6-benzyloxy-2,5,7,8-tetramethylchroman-2-ylmethyl methanesulphonate (10 g) and 2-(ethyl amino)ethanol (40 ml) by an analogous procedure to that described in preparation 1.

¹H NMR (CDCl₃, 200 MHz): δ1.05 (t, J=7.2 Hz, 3H), 1.22 (s, 3H), 1.65–1.80 (m, 1H), 1.85–2.05 (m, 1H), 2.10 (s, 3H), 2.17 (s, 3H), 2.22 (s, 3H), 2.65–2.85 (m, 8H), 3.45–3.70 (m, 2H), 4.70 (s, 2H), 7.30–7.65 (m, 5H).

Preparation 5

2-[N-(5-Benzyloxy-2,3-dihydro-2,2,4,6,7-pentamethyl-1-benzofuran -3ylmethyl)-N-methylamino]ethanol

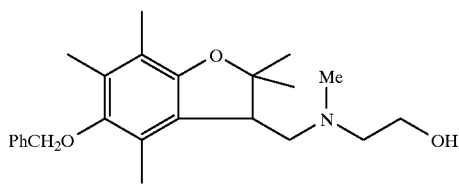

The title compound was prepared from 5-benzyloxy-2,3-dihydro-2,2,4,6,7-pentamethyl-1-benzofuran-3-ylmethyl methanesulphonate (5 g) and 2-(methylamino)ethanol (10 ml) by an analogous procedure to that described in preparation 1.

¹H NMR (CDCl₃, 200 MHz) δ1.33 (s, 3H), 1.58 (s, 3H), 2.08 (s, 3H), 2.19 (s, 3H), 2.22 (s, 3H), 2.34 (s, 3H), 2.39 (m, 2H), 2.71 (m, 2H), 3.08 (m, 1H), 3.62 (m, 2H), 4.73 (s, 2H), 7.43 (m, 5H).

Preparation 6

2-[N-Methyl-N-(5-methyl-2-phenyl-4-oxazolyl)methylamino]ethanol

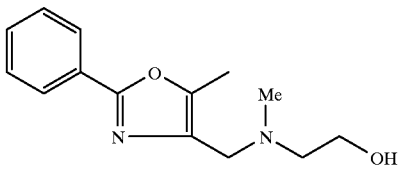

The title compound was prepared from 4-chloromethyl-5-methyl-2-phenyloxazole (10 g) and 2-(methylamino)ethanol (36 ml) by an analogous procedure to that described in preparation 1.

¹H NMR (CDCl₃, 200 MHz): δ2.32 (s, 3H), 2.35 (s, 3H), 2.61 (t, J=5.4 Hz, 2H), 3.1 (bs, 1H), 3.51 (s, 2H), 3.64 (t, J=5.0 Hz, 2H), 7.39 (m, 3H), 7.96 (m, 2H).

Preparation 7

2-[N-Methyl-N-(2-pyridylmethyl)amino]ethanol

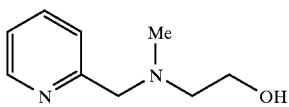

The title compound was prepared from 2-picolyl chloride (3 g) and 2-(methylamino)ethanol (19 ml) by an analogous procedure to that described in preparation 1.

¹H NMR (CDCl₃, 200 MHz): δ2.4 (s, 3H), 2.72 (t, J=5.2 Hz, 2H), 3.0 (bs, 1H), 3.68 (t, J=5.2 Hz, 2H), 3.8 (s, 2H), 7.22 (dd, J₁=12.7 Hz, J₂=8.0 Hz, 1H), 7.38 (d, J=7.8 Hz, 1H), 7.70 (t, J=8.0 Hz, 1H), 8.56 (d, J=4.2 Hz, 1H).

Preparation 8

2-(N-Benzyl-N-methylamino)ethanol

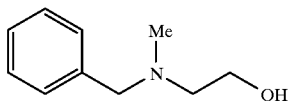

The title compound was prepared from benzyl bromide (4 g) and 2-(methylamino)ethanol (18.6 ml) by an analogous procedure to that described in preparation 1.

¹H NMR (CDCl₃, 200 MHz): δ2.25 (s, 3H), 2.6 (t, J=6.78 Hz, 2H), 2.8 (bs, 1H), 3.55 (s, 2H), 3.65 (t, J=6.78 Hz, 2H), 7.3 (s, 5H).

Preparation 9

2-[N-Methyl-N-(3-phenylpropyl)amino]ethanol

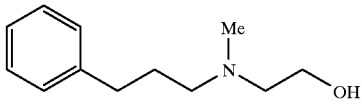

The title compound was prepared from 3-phenylpropyl methanesulphonate (4.5 g) and 2-(methylamino)ethanol (16.7 ml) by an analogous procedure to that described in preparation 1.

¹H NMR (CDCl₃, 200 MHz): δ1.8 (m, 2H), 2.3 (s, 3H), 2.4–2.7 (m, 6H), 3.6 (t, J=6.7 Hz, 2H), 3.95 (bs, 1H), 7.2 (m, 5H).

Preparation 10

2-[N-Methyl-N-(3-phenylprop-2-enyl)amino]ethanol

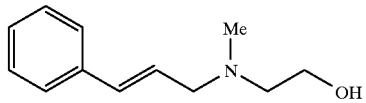

The title compound was prepared from 3-bromo-1-phenylprop-1-ene (0.77 g) and 2-(methylamino)ethanol (3.1 ml) by an analogous procedure to that described in preparation 1.

¹H NMR (CDCl₃, 200 MHz): δ2.35, (s, 3H), 2.7 (t, J=5.2 Hz, 2H), 3.3 (d, J=6.8 Hz, 2H), 3.7 (t, J=5.0 Hz, 2H), 3.95 (bs, 1H), 6.15–6.3 (m, 1H), 6.55 (d, J=15.8, 1H), 7.3 (m, 5H).

Preparation 11

2-[N-(6-Benzyloxy-2,5,7,8-tetramethylchroman-2-ylmethyl)-N-methylamino]ethyl bromide

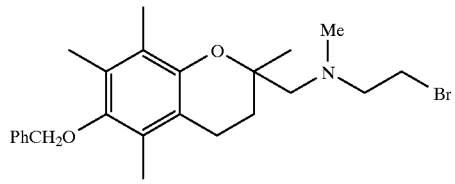

To an ice cooled solution of the product obtained in the preparation 1 (3 g) and carbon tetrabromide (3.87 g) in dichloromethane (100 ml) was added triphenyl phosphine (3.66 g). The mixture was stirred for 1 h at room temperature. At the end of this time, the reaction mixture was washed with water, dried (CaCl₂) and concentrated. The crude product was purified by column chromatography using 20% EtOAc in petroleum ether as eluent to get 3.1 g of the title compound.

¹H NMR (CDCl₃, 200 MHz): δ1.25 (s, 3H), 1.65 (m, 1H), 2.0 (m, 1H), 2.1 (s, 3H), 2.18 (s, 3H), 2.2 (s, 3H), 2.48 (s, 3H), 2.6 (bs, 4H), 2.97 (m, 2H), 3.4 (t, J=6.45 Hz, 2H), 4.7 (s, 2H), 7.3–7.55 (m, 5H).

Preparation 12

2-[N-Benzyl-N-methylamino]ethyl chloride

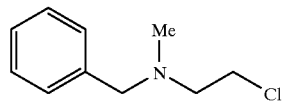

Thionyl chloride (2 ml) was added dropwise to a stirred, ice cooled solution of 2-[N-benzyl-N-methylamino]ethanol (4 g) obtained in preparation 8, in dry benzene (10 ml). The resulting mixture was stirred at 0° C. for 2 h and then diluted with ethyl acetate (40 ml), washed with saturated aqueous sodium bicarbonate solution (2×25 ml), water (50 ml), brine (50 ml) and dried. The ethyl acetate layer was evaporated and the residue was chromatographed on silica gel with 20% ethyl acetate in petroleum ether as eluent to give 2.6 g of the title compound.

¹H NMR (CDCl₃, 200 MHz): δ2.3 (s, 3H), 2.75 (t, J=6.5 Hz, 2H), 3.55–3.65 (t, J=6.5 Hz, 2H), 3.6 (s, 2H), 7.35 (s, 5H).

Preparation 13

2-[N-(6-Benzyloxy-2,5,7,8-tetramethylchroman-2ylmethyl)-N -methylamino]ethyl chloride

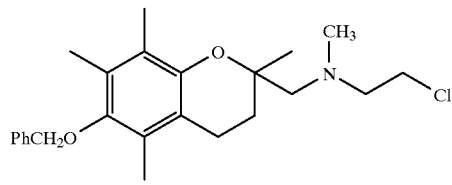

The title compound was prepared from 2-[N-(6-benzyloxy-2,5,7,8-tetramethylchroman-2-ylmethyl)-N-methylamino]ethanol (4 g), obtained in the preparation 1, and thionyl chloride (2.5 ml) by a similar procedure to that used in preparation 12.

¹H NMR (CDCl₃, 200 MHz): δ1.25 (s, 3H), 1.6–1.8 (m, 1H), 1.9–2.07 (m, 1H ), 2.10 (s, 3H), 2.17 (s, 3H), 2.22 (s, 3H), 2.49 (s, 3H), 2.55–2.75 (m, 4H), 2.94 (t, J=7.0 Hz, 2H), 3.60 (t, J=7.0 Hz, 2H), 4.69 (s, 2H), 7.3–7.6 (m, 5H).

Preparation 14

2-[N-(6-Hydroxy-2,5,7,8-tetramethylchroman-2-ylmethyl)-N-methhylamino]ethyl chloride

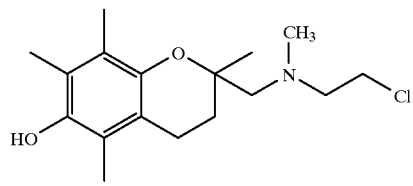

To a solution of 4 g of 2-[N-(6-benzyloxy-2,5,7,8-tetramethylchroman-2-ylmethyl) -N-methylamino]ethyl chloride, obtained in preparation 13, in 120 ml of AcOH was added 40 ml of concentrated hydrochloric acid. The resulting mixture was heated at 60° C. for 1 h. At the end of this time, the solvent was removed under reduced pressure and the residue was diluted with EtOAc and washed with saturated aqueous NaHCO₃ solution followed by brine. The organic layer was dried over anhydrous sodium sulphate and the solvent was removed by distillation under reduced pressure to give 3 g of the title compound.

¹H NMR (CDCl₃, 200 MHz): δ1.25 (s, 3H), 1.55–1.80 (m, 1H), 1.85–2.08 (m, 1H), 2.15 (s, 6H), 2.19 (s, 3H), 2.49 (s, 3H), 2.55–2.75 (m, 4H), 2.8–3.0 (m, 2H), 3.60 (t, J=7.2 Hz, 2H).

Preparation 15

2-[N-[6-Acetoxy-2,5,7,8-tetramethylchroman-2-ylmethyl)N-methylamino]ethyl chloride

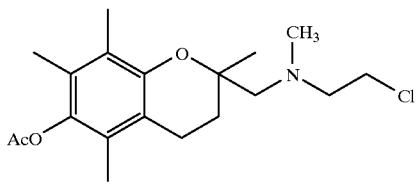

To an ice cold solution of the product obtained in the preparation 14 (20 g) and triethylamine (18 ml) in dichloromethane (100 ml), acetyl chloride (5.5 ml) was added and the mixture was stirred for 5 h at room temperature. At the end of this time the reaction mixture was washed with water, dried (CaCl$_2$) and concentrated. The crude product was purified by column chromatography using 30% EtOAc in petroleum ether as eluent to get 21 g of the title compound.

$^1$H NMR (CDCl$_3$, 200 MHz): δ1.21 (s, 3H), 1.60–1.80 (m, 1H), 1.85–2.05 (m, 1H), 1.98 (s, 3H), 2.02 (s, 3H), 2.08 (s, 3H), 2.32 (s, 3H), 2.44 (s, 3H), 2.55–2.75 (m, 4H), 2.90 (m, 2H), 3.55 (t, J=7 Hz, 2H).

Preparation 16

2-[N-[2-(6-Benzyloxy-2,5,7,8-tetramethylchroman-2yl) ethyl]-N-methylamino]ethyl chloride

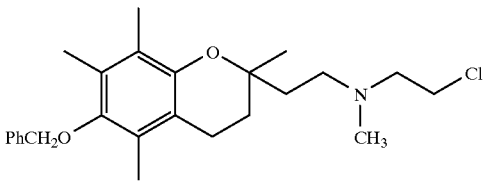

The title compound was prepared from the product obtained in preparation 2 (1 g) and thionyl chloride (1.5 ml) by a similar procedure to that used in preparation 12.

$^1$H NMR (CDCl$_3$, 200 MHz): δ1.25 (s, 3H), 1.85 (m, 4H), 2.1 (s, 3H), 2.15 (s, 3H), 2.25 (s, 3H), 2.35 (s, 3H), 2.55–2.85 (m, 6H), 3.55 (t, J=6.4 Hz, 2H), 4.7 (s, 2H), 7.3–7.6 (m, 5H).

Preparation 17

2-[N-(6-Benzyloxy-2,5,7,8-tetramethylchroman-2ylmethyl)amino]ethyl chloride

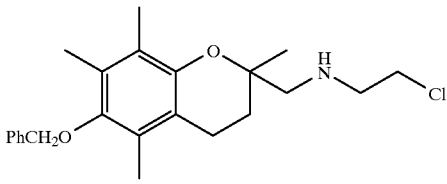

The title compound was prepared from 2-[N-(6-benzyloxy-2,5,7,8-tetramethylchroman-2-ylmethyl)amino]ethanol (10 g), obtained in preparation 3 and thionyl chloride (6 ml) by a similar procedure to that described in preparation 12.

$^1$H NMR (CDCl$_3$, 200 MHz): δ1.30 (s, 3H), 1.70–1.90 (m, 1H), 1.95–2.05 (m, 1H), 2.11 (s, 3H), 2.18 (s, 3H), 2.22 (s, 3H), 2.64 (t, J=6.8 Hz, 2H), 2.81 (s, 2H), 3.05 (t, J=5.6 Hz, 2H), 3.69 (t, J=5.6 Hz, 2H), 4.70 (s, 2H), 7.30–7.55 (m, 5H).

Preparation 18

2-[N-(6-Benzyloxy-2,5,7,8-tetramethylchroman-2-ylmethyl)-N -ethylamino]ethyl chliride

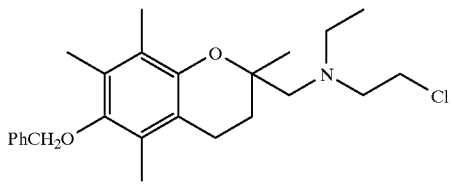

The title compound was prepared from 2-[N-(6-benzyloxy-2,5,7,8-tetramethylchroman-2-ylmethyl)-N-ethylamino]ethanol (10 g), obtained in preparation 4 and thionyl chloride (6 ml) by a similar procedure to that used in preparation 12.

$^1$H NMR (CDCl$_3$, 200 MHz): δ1.05 (t, J=7.2 Hz, 3H), 1.21 (s, 3H), 1.60–1.75 (m, 1H), 1.90–2.05 (m, 1H), 2.11 (s, 3H), 2.18 (s, 3H), 2.24 (s, 3H), 2.65–2.85 (m, 6H), 2.95–3.10 (m, 2H), 3.54 (t, J=7.6 Hz, 2H), 4.71 (s, 2H), 7.35–7.65 (m, 5H).

Preparation 19

2-[N-(5-Benzyloxy-2,3-dihydro-2,2,4,6,7-pentamethyl-1-benzofuran -3ylmethyl)-N-methylamino]ethyl chloride

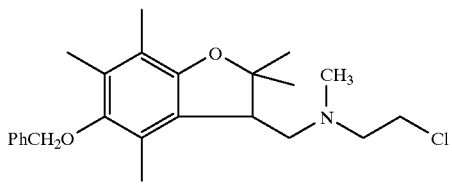

The title compound was prepared from 2-[N-(5-benzyloxy-2,3-dihydro-2,2,4,6,7-pentamethyl-1-benzofuran-3-ylmethyl)-N-methylamino]ethanol (2.7 g), obtained in preparation 5 and thionyl chloride (2.5 ml) by a similar procedure to that used in preparation 12.

$^1$H NMR (CDCl$_3$, 200 MHz): δ1.33 (s, 3H), 1.59 (s, 3H), 2.08 (s, 3H), 2.19 (s, 3H), 2.21 (s, 3H), 2.23 (s, 3H), 2.70 (m, 2H), 2.81 (m, 2H), 3.05 (m, 1H), 3.53 (t, J=5.5 Hz, 2H), 4.71 (s, 2H), 7.43 (m, 5H).

Preparation 20

2-[N-Methyl-N-(5-methyl-2-phenyl-4-oxazolyl)methylamino]ethyl chloride

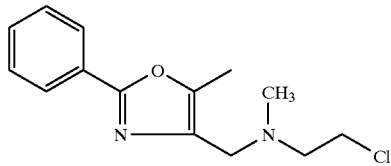

The title compound was prepared from 2-[N-Methyl-N-(5-methyl-2-phenyl-4-oxazolyl)methylamino]ethanol (10 g), obtained in preparation 6 and thionyl chloride (9 ml) by a similar procedure to that used in preparation 12.

$^1$H NMR (CDCl$_3$, 200 MHz): δ2.35 (s, 3H), 2.38 (s, 3H), 2.83 (t, J=7.2 Hz, 2H), 3.55 (s, 2H), 3.65 (t, J=7.0 Hz, 2H), 7.41 (m, 3H), 8.02 (m, 2H).

Preparation 21

2-[N-Methyl-N-(3-phenylpropyl)amino]ethyl chloride

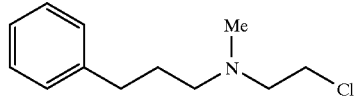

The title compound was prepared from 2-[N-methyl-N-(3-phenylpropyl)amino]ethanol (2 g), obtained in preparation 9 and thionyl chloride (3.8 ml) by a similar procedure to that used in preparation 12.

$^1$H NMR (CDCl$_3$, 200 MHz): δ1.7–1.95 (m, 2H), 2.35 (s, 3H), 2.45 (t, J=6.6 Hz, 2H), 2.6–2.8 (m, 4H), 3.55 (t, J=6.6 Hz, 2H), 7.25 (m, 5H).

Preparation 22

2-[N-Methyl-N-(3-phenylprop-2-enyl)amino]ethyl chloride

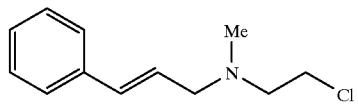

The title compound was prepared from 2-[N-methyl-N-(3-phenylprop-2-enyl)amino]ethanol (5.8 g), obtained in preparation 20 and thionyl chloride (13.3 ml) by a similar procedure to that used in preparation 12.

$^1$H NMR (CDCl$_3$, 200 MHz): δ2.4 (s, 3H), 2.80 (t, J=6.8 Hz, 2H), 3.3 (d, J=8.6 Hz, 2H), 3.65 (t, J=7.0 Hz, 2H), 6.15–6.35 (m, 1H), 6.65 (d, J=15.8 Hz, 1H), 7.2–7.45 (m, 5H).

Preparation 23

4-[2-[N-(6-Benzyloxy-2,5,7,8-tetramethylchroman-2-ylmethyl)]-N-methylamino]ethoxy]benzaldehyde

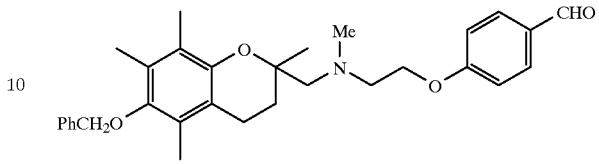

A solution of 9.4 g of the product obtained in the preparation 1 in 50 ml of dry N,N-dimethylformamide was added dropwise while cooling, to a suspension of 1.7 g (50% w/w oil dispersion) of sodium hydride in 20 ml of dry DMF. The mixture was then stirred for 1 h at room temperature, after which 3.9 g of 4-fluorobenzaldehyde was added dropwise at room temperature. The resulting mixture was then stirred at room temperature for 2 h. At the end of this time, water was added to the reaction mixture. The mixture was extracted with ethyl acetate and dried over anhydrous sodium sulphate. The solvent was removed by distillation under reduced pressure to give 10.5 g of the crude compound which was chromatographed on silicagel using 10 to 20% (gradient elution) of ethyl acetate in petroleum ether to afford the pure compound.

$^1$H NMR (CDCl$_3$, 200 MHz): δ1.25 (s, 3H), 1.65 (m, 1H), 2.0 (m, 1H), 2.1 (s, 3H), 2.18 (s, 3H), 2.2 (s, 3H), 2.5 (s, 3H), 2.55–2.85 (m, 4H), 3.05 (m, 2H), 4.19 (t, J=5.8 Hz, 2H), 4.7 (s, 2H), 6.98 (d, J=8.6 Hz, 2H), 7.4 (m, 5H), 7.8 (d, J=8.8 Hz, 2H), 9.85 (s, 1H).

Preparation 24

4-[2-[N-[2-(6-Benzyloxy-2,5,7,8-tetramethylchroman-2-yl)ethyl]-N-methylamino]ethoxy]benzaldehyde

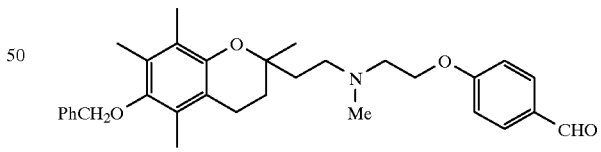

The title compound was prepared from 5.4 g of the product obtained in the preparation 2 and 4-fluorobenzaldehyde (1.8 g) in a similar manner to that described in preparation 23.

$^1$H NMR (CDCl$_3$, 200 MHz): δ1.3 (s, 3H), 1.7–1.95 (m, 4H), 2.1 (s, 3H), 2.15 (s, 3H), 2.2 (s, 3H), 2.4 (s, 3H), 2.55–2.8 (m, 4H), 2.85 (t, J=6.2 Hz, 2H), 4.15 (t, J=6.2 Hz, 2H), 4.7 (s, 2H), 7.0 (d, J=6.9 Hz, 2H), 7.3–7.55 (m, 5H), 7.8 (d, J=6.9 Hz, 2H), 9.9 (s, 1H).

Preparation 25

4-[2-[N-(6-Benzyloxy-2,5,7,8-tetramethylchroman-2ylmethyl)amino]ethoxy]benzaldehyde

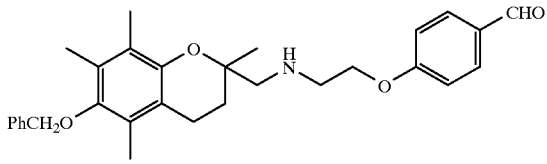

The title compound was prepared from 2-[N-(6-benzyloxy-2,5,7,8-tetramethylchroman-2-ylmethyl)amino]ethanol (5 g) obtained in preparation 3 and 4-fluorobenzaldehyde (2.1 ml) by an analogous procedure to that described in preparation 23.

$^1$H NMR (CDCl$_3$, 200 MHz): δ1.30 (s, 3H), 1.65–1.85 (m, 1H), 1.90–2.05 (m, 1H), 2.10 (s, 3H), 2.17 (s, 3H), 2.21 (s, 3H), 2.64 (t, J=7.0 Hz, 2H), 2.85 (s, 2H), 3.10 (t, J=5.2 Hz, 2H), 4.17 (t, J=5 Hz, 2H), 4.7 (s, 2H), 7.0 (d, J=8.6 Hz, 2H), 7.3–7.6 (m, 5H), 7.83 (d, J=8.8 Hz, 2H), 9.90 (s, 1H).

Preparation 26

4-[2-[N-(6-Benzyloxy-2,5,7,8-tetramethylchroman-2-ylmethyl)-N-ethylamino]ethoxy]benzaldehyde

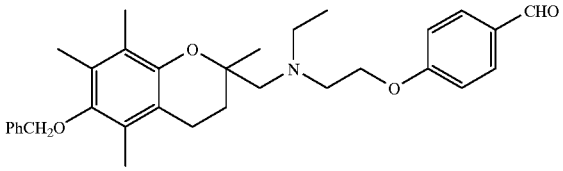

To a mixture of 2-[N-(6-benzyloxy-2,5,7,8-tetramethylchroman-2-ylmethyl)-N-ethylamino]ethyl chloride (3.9 g) obtained in preparation 18, and 4-hydroxy benzaldehyde (1.3 g) in dry DMF, K$_2$CO$_3$ (4.8 g) was added and the mixture was stirred at 80° C. for 6 h. At the end of this time, the reaction mixture was cooled, added water and extracted with EtOAc. The EtOAc extract was washed with 5% aqueous Na$_2$CO$_3$ solution, followed by brine and dried over anhydrous sodium sulphate. The solvent was then removed by distillation under reduced pressure to give 4.2 g of the crude compound. This was chromatographed on silicagel using 10 to 20% (gradient elution) of ethyl acetate in petroleum ether to afford the pure compound.

$^1$H NMR (CDCl$_3$, 200 MHz): δ1.07 (t, J=7.0 Hz, 3H), 1.23 (s, 3H), 1.60–1.80 (m, 1H), 1.9–2.05 (m, 1H), 2.06 (s, 3H), 2.18 (s, 3H), 2.20 (s, 3H), 2.55–2.85 (m, 6H), 3.09 (t, J=6.2 Hz, 2H), 4.13 (t, J=6.2 Hz, 2H), 4.70 (s, 2H), 6.95 (d, J=8.8 Hz, 2H), 7.30–7.60 (m, 5H), 7.80 (d, J=8.6 Hz, 2H), 9.90 (s, 1H)

Preparation 27

4-[2-[N-(5-Benzyloxy-2,3-dihydro-2,2,4,6,7-pentamethyl-1-benzofuran-3-ylmethyl)-N-methylamino]ethoxy]benzaldehyde

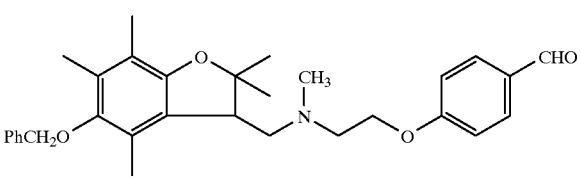

The title compound was prepared from 2-[N-(5-benzyloxy-2,3-dihydro-2,2,4,6,7-pentamethyl-1-benzofuran-3-ylmethyl)-N-methylamino]ethyl chloride (4 g) obtained in preparation 19 and 4-hydroxybenzaldehyde (1.2 g) in a similar manner to that described in preparation 26.

$^1$H NMR (CDCl$_3$, 200 MHz): δ1.36 (s, 3H), 1.61 (s, 3H), 2.11 (s, 3H), 2.22 (s, 3H), 2.27 (s, 3H), 2.41 (s, 3H), 2.76 (m, 2H), 2.96 (m, 2H), 3.10 (m, 1H), 4.13 (t, J=5.7 Hz, 2H), 4.73 (s, 2H), 7.03 (d, J=8.7 Hz, 2H), 7.43 (m, 5H), 7.85 (d, J=8.6 Hz, 2H), 9.91 (s, 1H).

Preparation 28

4-[2-[N-Methyl-N-(5-methyl-2-phenyl-4-oxazolyl)methylamino]ethoxy]benzaldehyde

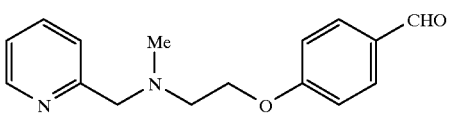

The title compound was prepared from 2-[N-methyl-N-(5-methyl-2-phenyl-4-oxazolyl)methylamino]ethanol (2.93 g) obtained in preparation 6 and 4-fluorobenzaldehyde (6.5 ml) by an analogous procedure to that described in preparation 23.

$^1$H NMR (CDCl$_3$, 200 MHz): δ2.45 (2s, 6H), 3.0 (m, 2H), 3.65 (s, 2H), 4.25 (t, J=5.6 Hz, 2H), 7.0 (d, J=8.6 Hz, 2H), 7.45 (m, 3H), 7.85 (d, J=8.8 Hz, 2H), 8.05 (m, 2H), 9.85 (s, 1H).

Preparation 29

4-[2-[N-Methyl-N-(2-pyridylmethyl)amino]ethoxy]benzaldehyde

The title compound was prepared from 2-[N-methyl-N-(2-pyridylmethyl)amino]ethanol (2.5 g) obtained in preparation 7 and 4-fluorobenzaldehyde (2.4 ml) by an analogous procedure to that described in preparation 23.

$^1$H NMR (CDCl$_3$, 200 MHz): δ2.45 (s, 3H), 2.95 (m, 2H), 3.85 (s, 2H), 4.2 (t, J=6.25 Hz, 2H), 7.0 (d, J=8.3 Hz, 2H), 7.2 (m, 1H), 7.45 (d, J=8.3 Hz, 1H), 7.77 (t, J=6.2 Hz, 1H), 7.85 (d, J=8.3 Hz, 2H), 8.55 (m, 1H), 9.9 (s, 1H).

Preparation 30

4-[2-(N-Benzyl-N-methylamino)ethoxy] benzaldehyde

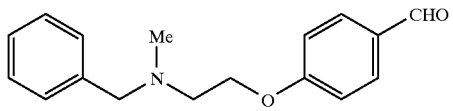

The title compound was prepared from 2-(N-benzyl-N-methylamino)ethanol (2.5 g) obtained in example 8 and 4-fluorobenzaldehyde (2 ml) by an analogous procedure to that described in preparation 23.

$^1$H NMR (CDCl$_3$, 200 MHz): δ2.4 (s, 3H), 2.85 (t, J=6.25 Hz, 2H), 3.68 (s, 2H), 4.15 (t, J=6.25 Hz, 2H), 7.0 (d, J=8.3 Hz, 2H), 7.35 (m, 5H), 7.85 (d, J=8.3 Hz, 2H), 9.9 (s, 1H).

Preparation 31

4-[2-[N-Methyl-N-(3-phenylpropyl)amino]ethoxy] benzaldehyde

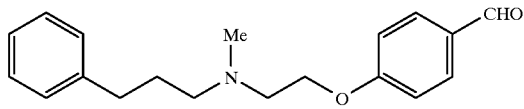

The title compound was prepared from 2-[N-Methyl-N-(3-phenylpropyl)amino]ethyl chloride (7 g) obtained in preparation 21 and 4-hydroxybenzaldehyde(6 g) in a similar manner to that described in preparation 26.

$^1$H NMR (CDCl$_3$, 200 MHz): δ1.8–2.1 (m, 2H), 2.45 (s, 3H), 2.5–2.8 (m, 4H), 2.9 (m, 2H), 4.2 (t, J=6.25 Hz, 2H), 7.0 (d, J=8.5 Hz, 2H), 7.1–7.4 (m, 5H), 7.85 (d, J=8.5 Hz, 2H), 9.9 (s, 1H)

Preparation 32

4-[2-[N-Methyl-N-(3-phenylprop-2-enyl)amino] ethoxy]benzaldehyde

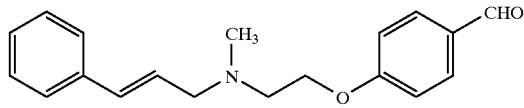

The title compound was prepared from 2-[N-Methyl-N-(3-phenylprop-2-enyl)amino]ethyl chloride (4 g), obtained in preparation 22 and 4-hydroxy benzaldehyde (3.4 g) in a similar manner to that described in preparation 26.

$^1$H NMR (CDCl$_3$, 200 MHz): δ2.41 (s, 3H), 2.89 (t, J=5.6 Hz, 2H), 3.29 (d, J=6.6 Hz, 2H), 4.18 (t, J=5.8 Hz, 2H), 6.20–6.40 (m, 1H), 6.55 (d, J=15.8 Hz, 1H), 7.02 (d, J=8.4 Hz, 2H), 7.15–7.50 (m, 5H), 7.82 (d, J=8.6 Hz, 2H), 9.90 (s, 1H).

Preparation 33

4-[2-[N-(6-Benzyloxy-2,5,7,8-tetramethylchroman-2-ylmethyl)N-methylamino]ethoxy]nitro benzene

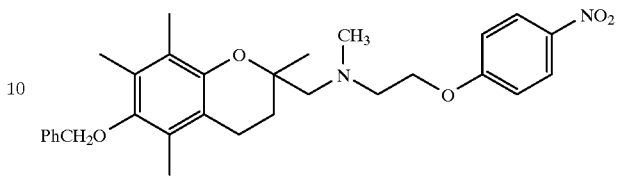

A stirred mixture of 2-[N-(6-benzyloxy-2,5,7,8-tetramethylchroman-2-ylmethyl) -N-methylamino]ethyl chloride (4 g), obtained in preparation 13, 4-nitrophenol (1.4 g) and K$_2$CO$_3$ (3.5 g) in anhydrous DMF (20 ml) was heated at 80° C. for 4 h. At the end of this time, the reaction mixture was cooled, water was added and the mixture was extracted with EtOAc. The extract was washed with 5% aqueous Na$_2$CO$_3$ followed by brine and dried (over Na$_2$SO$_4$). The solvent was removed by distillation under reduced pressure to give 4.5 g of the crude product. The crude product was chromatographed on silicagel using 10 to 20% (gradient elution) of ethyl acetate in petroleum ether to afford the pure compound.

$^1$H NMR (CDCl$_3$, 200 MHz): δ1.25 (s, 3H), 1.60–1.80 (m, 1H), 1.95–2.05 (m, 1H), 2.06 (s, 3H), 2.17 (s, 3H), 2.20 (s, 3H), 2.52 (s, 3H), 2.55–2.75 (m, 4H), 3.04 (m, 2H), 4.15 (m, 2H), 4.68 (s, 2H), 6.92 (d, J=9.2 Hz, 2H), 7.35–7.60 (m, 5H), 8.17 (d, J=9Hz, 2H).

Preparation 34

4-[2-[N-(6-Acetoxy-2,5,7,8-tetramethylchroman-2-ylmethyl)-N-methylamino]ethoxy]nitro benzene

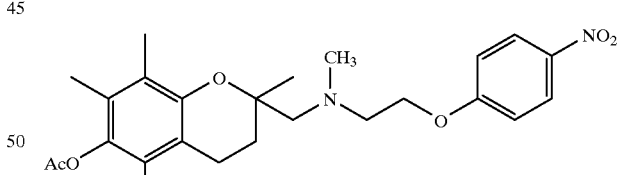

The title compound was prepared from 2-[N-(6-acetoxy-2,5,7,8-tetramethylchroman-2-ylmethyl) -N-methylamino] ethyl chloride (2.5 g), obtained in preparation 15 and 4-nitrophenol (1.1 g) in a similar manner to that described in preparation 33.

$^1$H NMR (CDCl$_3$, 200 MHz): δ1.23 (s, 3H), 1.60–1.80 (m, 1H), 1.95–2.05 (m, 1H), 1.97 (s, 3H), 2.0 (s, 3H), 2.05 (s, 3H), 2.33 (s, 3H), 2.50 (s, 3H), 2.60–2.80 (m, 4H), 3.02 (t, J=5.6 Hz, 2H), 4.14 (t, J=5.8 Hz, 2H), 6.89 (d, J=9.2 Hz, 2H), 8.16 (d, J=9.2 Hz, 2H).

Preparation 35

4-[2-[N-[2-(6-Benzyloxy-2,5,7,8-tetramethylchroman-2-yl)ethyl]-N-methylamino]ethoxy]nitrobenzene

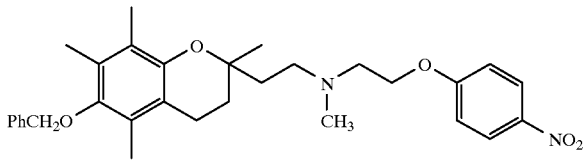

The title compound was prepared from 2-[N-[2-(6-benzyloxy-2,5,7,8-tetramethylchroman-2-yl)ethyl]-N-methylamino]ethyl chloride (4.2 g), obtained in preparation 16 and 4-nitrophenol (2 g) in a similar manner to that described in preparation 33.

$^1$H NMR (CDCl$_3$, 200 MHz): δ1.27 (s, 3H), 1.6–2.05 (m, 4H), 2.08 (s, 3H), 2.16 (s, 3H), 2.20 (s, 3H), 2.35 (s, 3H), 2.50–2.70 (m, 4H), 2.83 (t, J=5.8 Hz, 2H), 4.12 (t, J=5.8 Hz, 2H), 4.68 (s, 2H), 6.95 (d, J=9.2 Hz, 2H), 7.3–7.6 (m, 5H), 8.19 (d, J=9.2 Hz, 2H).

Preparation 36

4-[2-[N-(6-Benzyloxy-2,5,7,8-tetramethylchroman-2-ylmethyl)-N-ethylamino]ethoxy]nitro benzene

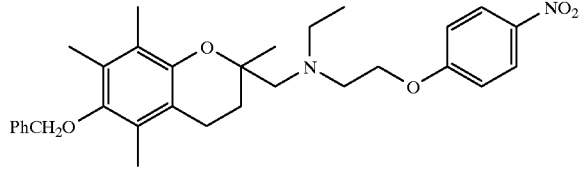

The title compound was prepared from 2-[N-(6-benzyloxy-2,5,7,8-tetramethylchroman-2-ylmethyl)-N-ethylamino]ethyl chloride (5 g), obtained in preparation 18 and 4-nitrophenol (1.7 g) in a similar manner to that described in preparation 33.

$^1$H NMR (CDCl$_3$, 200 MHz): δ1.06, (t, J=7.2 Hz, 3H), 1.21 (s, 3H), 1.50–1.80 (m, 1H), 1.95–2.05 (m, 1H), 2.04 (s, 3H), 2.17 (s, 3H), 2.19 (s, 3H), 2.55–2.85 (m, 6H), 3.09 (t, J=6.4 Hz, 2H), 4.12 (t, J=6.2 Hz, 2H), 4.70 (s, 2H), 6.90 (d, J=9.2 Hz, 2H), 7.30–7.60 (m, 5H), 8.15 (d, J=9.0 Hz, 2H).

Preparation 37

4-[2-[N-(5-Benzyloxy-2,3-dihydro-2,2,4,6,7-pentamethyl-1-benzofuran-3-ylmethyl)-N-methylamino]ethoxy]nitrobenzene

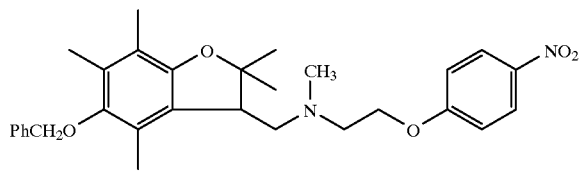

The title compound was prepared from 2-[N-(5-benzyloxy-2,3-dihydro-2,2,4,6,7-pentamethyl-1-benzofuran-3-ylmethyl)-N-methylamino]ethyl chloride (10 g), obtained in preparation 19 and 4-nitrophenol (5 g) in a similar manner to that described in preparation 33.

$^1$H NMR (CDCl$_3$, 200 MHz): δ1.35 (s, 3H), 1.60 (s, 3H), 2.10 (s, 3H), 2.22 (s, 3H), 2.25 (s, 3H), 2.40 (s, 3H), 2.74 (m, 2H), 2.93 (m, 2H), 3.08 (m, 1H), 4.09 (m, 2H), 4.70 (s, 2H), 6.92 (d, J=9.0 Hz, 2H), 7.43 (m, 5H), 8.19 (d, J=9.0 Hz, 2H).

Preparation 38

4-[2-[N-(6-Benzyloxy-2,5,7,8-tetramethylchroman-2-ylmethyl)-N-methylamino]ethoxy]aniline

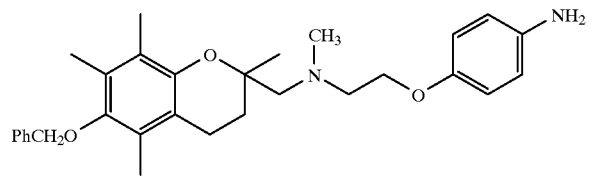

4-[2-[N-(6-benzyloxy-2,5,7,8-tetramethylchroman-2-ylmethyl)-N-methylamino]ethoxy]nitrobenzene (1 g) obtained in preparation 33, was dissolved in EtOAc (6 ml) and was reduced with hydrogen (60 psi) in the presence of 10% palladium on charcoal (100 mg) at ambient temperature until hydrogen uptake (nearly 8 h) ceased. The solution was filtered through a bed of celite, the filter pad was washed exhaustively with EtOAc. The combined filtrate was evaporated to dryness under reduced pressure. The crude product was chromatographed on silica gel using 2 to 10% (gradient elution) of methanol in chloroform to afford 0.9 g of the title compound.

$^1$H NMR (CDCl$_3$, 200 MHz): δ1.28 (s, 3H), 1.65–1.90 (m, 1H), 1.95–2.10 (m, 1H), 2.11 (s, 3H), 2.18 (s, 3H), 2.23 (s, 3H), 2.53 (s, 3H), 2.6–2.8 (m, 4H), 3.0 (m, 2H), 4.05 (t, J=6.2 Hz, 2H), 4.71 (s, 2H), 6.63 (d, J=8.8 Hz, 2H), 6.75 (d, J=8.8 Hz, 2H), 7.35–7.65 (m, 5H).

Preparation 39

4-[2-[N-(6-Acetoxy-2,5,7,8-tetramethylchroman-2-ylmethyl)-N-methylamino]ethoxy]aniline

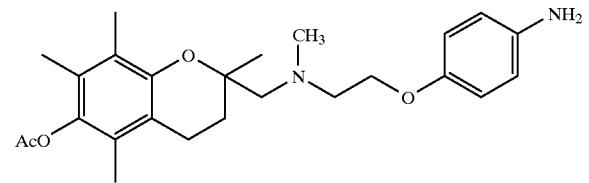

The title compound was prepared from 4-[2-[N-(6-acetoxy-2,5,7,8-tetramethylchroman-2-ylmethyl)-N-methylamino]ethoxy]nitrobenzene (10 g), obtained in preparation 34, by a similar procedure to that described in preparation 38.

$^1$H NMR (CDCl$_3$, 200 MHz): δ1.25 (s, 3H), 1.6–1.8 (m, 1H), 1.90–2.05 (m, 1H), 1.99 (s, 3H), 2.02 (s, 3H), 2.07 (s, 3H), 2.34 (s, 3H), 2.45 (s, 3H), 2.55–2.70 (m, 4H), 2.95 (m, 2H), 4.05 (m, 2H), 6.62 (d, J=8.8 Hz, 2H), 6.73 (d, J=8.6 Hz, 2H).

Preparation 40

4-[2-[N-[2-(6-Benzyloxy-2,5,7,8-tetramethylchroman-2-yl)ethyl]-N-methylamino]ethoxy]aniline

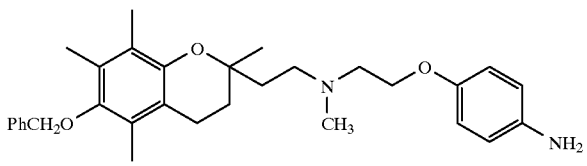

The title compound was prepared from 4-[2-[N-[2-(6-benzyloxy-2,5,7,8-tetramethylchroman-2-yl)ethyl]-N-methylamino]ethoxy]nitrobenzene (2 g), obtained in preparation 35, by a similar procedure to that described in preparation 38.

$^1$H NMR (CDCl$_3$, 200 MHz): δ1.26 (s, 3H), 1.65–2.05 (m, 4H), 2.08 (s, 3H), 2.25 (s, 3H), 2.20 (s, 3H), 2.34 (s, 3H), 2.50–2.75 (m, 4H), 2.79 (t, J=6.0 Hz, 2H), 3.99 (t, J=6.2 Hz, 2H), 4.68 (s, 2H), 6.62 (d, J=9.0 Hz, 2H), 6.73 (d, J=8.8 Hz, 2H), 7.30–7.60 (m, 5H).

Preparation 41

4-[2-[N-(6-Benzyloxy-2,5,7,8-tetramethylchroman-2-ylmethyl)-N-ethylamino]ethoxy]aniline

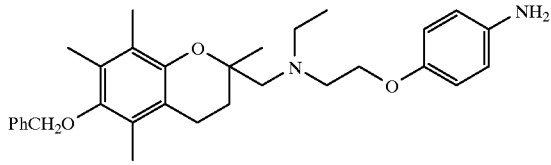

The title compound was prepared from 4-[2-[N-(6-benzyloxy-2,5,7,8-tetramethylchroman-2-yl methyl)-N-ethylamino]ethoxy]nitrobenzene (20 g), obtained in preparation 36, by a similar procedure to that described in preparation 38.

$^1$H NMR (CDCl$_3$, 200 MHz): δ1.06 (t, J=7.2 Hz, 3H), 1.24 (s, 3H), 1.55–1.80 (m, 1H), 1.90–2.05 (m, 1H), 2.08 (s, 3H), 2.18 (s, 3H), 2.22 (s, 3H), 2.50–2.90 (m, 6H), 3.01 (t, J=6.0 Hz, 2H), 3.99 (t, J=6.2 Hz, 2H), 4.7 (s, 2H), 6.62 (d, J=8.4 Hz, 2H), 6.73 (d, J=8.8 Hz, 2H), 7.30–7.65 (m, 5H).

Preparation 42

4-[2-[N-(5-Benzyloxy-2,3-dihydro-2,2,4,6,7-pentamethyl-1-benzofuran-3-ylmethyl)-N-methylamino]ethoxy]aniline

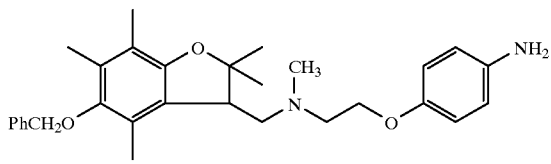

The title compound was prepared from 4-[2-[N-(5-benzyloxy-2,3,-dihydro-2,2,4,6,7-pentamethyl-1-benzofuran-3-ylmethyl)-N-methylamino]ethoxy]nitro benzene (10 g), obtained in preparation 37, by a similar procedure to that described in preparation 38.

$^1$H NMR (CDCl$_3$, 200 MHz): δ1.34 (s, 3H), 1.62 (s, 3H), 2.08 (s, 3H), 2.22 (s, 3H), 2.27 (s, 3H), 2.38 (s, 3H), 2.74 (m, 2H), 2.93 (m, 2H), 3.10 (m, 1H), 3.98 (t, J=5.5 Hz, 2H), 4.70 (s, 2H), 6.62 (d, J=8.0 Hz, 2H), 6.73 (d, J=8.0 Hz, 2H), 7.40 (m, 5H).

Preparation 43

4-[2-(N-Benzyl-N-methylamino)ethylthio]aniline

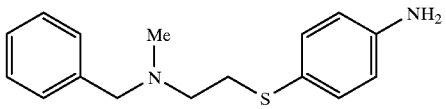

A stirred mixture of 2-(N-benzyl-N-methylamino)ethyl chloride (2 g) obtained in preparation 12, 4-aminothiophenol (1.25 g) and potassium carbonate (4.1 g) was heated at reflux for 6 h in dry acetone (15 ml); After cooling, the reaction mixture was filtered and the filtrate was evaporated to dryness. The residue was chromatographed on silica gel with 10% ethyl acetate in pet. ether as eluent to give 1.2 g of the title compound.

$^1$H NMR (CDCl$_3$, 200 MHz): δ2.21 (s, 3H), 2.62 (dd, J$_1$=9.2 Hz, J$_2$=5.0 Hz, 2H), 2.92 (dd, J$_1$=9.1 Hz, J$_2$=6.6 Hz, 2H), 3.5 (s, 2H), 6.6 (d, J=8.6 Hz, 2H), 7.2 (d, J=8.4 Hz, 2H), 7.29 (s, 5H).

Preparation 44

Ethyl 2-boromo-3-[4-[2-(N-benzyl-N-methylamino)ethylthio]phenyl]propionate

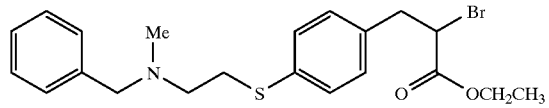

A solution of NaNO$_2$ (1.3 g) in H$_2$O (2.5 ml) was added dropwise to a stirred and ice cooled mixture of 4-[2-(N-benzyl-N-methylamino)ethylthio]aniline (5 g), obtained in preparation 43, aqueous HBr (48%, 12.7 ml), MeOH (17 ml) and acetone (42 ml) below 5° C. The solution was stirred at 5° C. for 30 min. and ethyl acrylate (12 ml) was added and the temperature was raised to 38° C. Powder Cu$_2$O (160 mg) was added in small portions to the vigorously stirred mixture. After the N$_2$ gas evolution has ceased, the reaction mixture was concentrated in vacuo. The residue was diluted with water, made alkaline with concentrated NH$_4$OH and extracted with EtOAc. The EtOAc extract was washed with brine, dried (Na$_2$SO$_4$) and concentrated in vacuo to give 3.7 g of the title compound.

$^1$H NMR (CDCl$_3$, 200 MHz): δ1.25 (t, J=6.7 Hz, 3H), 2.25 (s, 3H), 2.65 (m, 2H), 3.1 (m, 2H), 3.2 (dd, J$_1$=13.3 Hz, J$_2$=6.6 Hz, 1H), 3.45 (dd, J$_1$=13.5 Hz, J$_2$=6.7 Hz, 1H), 3.55 (s, 2H), 4.15 (q, J=6.7 Hz, 2H), 4.35 (t, J=6.7 Hz, 1H), 7.1 (d, J=8.3 Hz, 2H), 7.2 (d, J=8.3 Hz, 2H), 7.3 (s, 5H).

Preparation 45

Ethyl 2-bromo-3-[4-[2-[N-(6-benzyloxy-2,5,7,8-tetramethylchroman-2-ylmethyl)-N-methylamino]ethoxy]phenyl]propionate

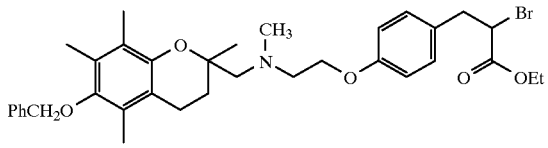

The title compound was prepared from 4-[2-[N-(6-benzyloxy-2,5,7,8-tetramethylchroman-2-ylmethyl)-N-methylamino]ethoxy]aniline (10 g), obtained in preparation 38, by a similar procedure to that described in preparation 44.

$^1$H NMR (CDCl$_3$, 200 MHz): δ1.10–1.40 (m, 6H), 1.60–1.80 (m, 1H), 1.90–2.05 (m, 1H), 2.08 (s, 3H), 2.16 (s, 3H), 2.20 (s, 3H), 2.51 (s, 3H), 2.55–2.75 (m, 4H), 3.0 (m, 2H), 3.10–3.25 (m, 1H), 3.30–3.50 (m, 1H), 4.0–4.25 (m, 4H), 4.28–4.40 (m, 1H), 4.70 (s, 2H), 6.80 (d, J=8.6 Hz, 2H), 7.10 (d, J=8.6 Hz, 2H), 7.30–7.60 (m, 5H).

Preparation 46

Ethyl 2-bromo-3-[4-[2-[N-(6-acetoxy-2,5,7,8-tetramethylchroman-2-ylmethyl)-N-methylamino]ethoxy]phenyl]propionate

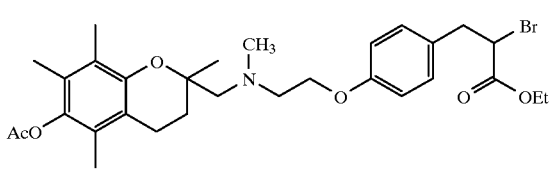

The title compound was prepared from 4-[2-[N-(6-acetoxy-2,5,7,8-tetramethylchroman-2-ylmethyl)-N-methylamino]ethoxy]aniline (5 g), obtained in preparation 39, by a similar procedure to that described in preparation 44.

$^1$H NMR (CDCl$_3$, 200 MHz): δ1.25 (m, 6H), 1.60–1.80 (m, 1H), 1.90–2.05 (m, 1H), 1.98 (s, 3H), 2.01 (s, 3H), 2.07 (s, 3H), 2.34 (s, 3H), 2.52 (s, 3H), 2.55–2.80 (m, 4H), 2.95–3.05 (m, 2H), 3.10–3.25 (m, 1H), 3.30–3.50 (m, 1H), 4.0–4.25 (m, 4H), 4.30–4.40 (m, 1H), 6.81 (d, J=8.6 Hz, 2H), 7.11 (d, J=8.4 Hz, 2H).

Preparation 47

Ethyl 2-bromo-3-[4-[2-[N-[2-(6-benzyloxy-2,5,7,8-tetramethylchroman-2-yl)ethyl]-N-methylamino]ethoxy]phenyl]propionate

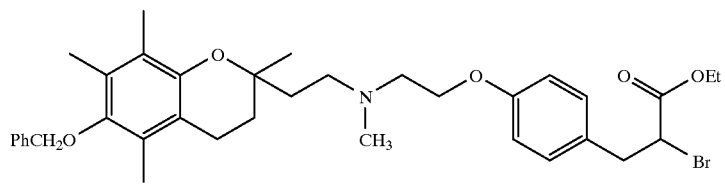

The title compound was prepared from 4-[2-[N-[2-(6-benzyloxy-2,5,7,8-tetramethylchroman-2-yl)ethyl]-N-methylamino]ethoxy]aniline (1 g), obtained in preparation 40, by a similar procedure to that described in preparation 44.

$^1$H NMR (CDCl$_3$, 200 MHz): δ1.10–1.35 (m, 6H), 1.65–2.0 (m, 4H), 2.08 (s, 3H), 2.16 (s, 3H), 2.20 (s, 3H), 2.36 (s, 3H), 2.55–2.90 (m, 6H), 3.10–3.25 (m, 1H), 3.30–3.45 (m, 1H), 4.0–4.40 (m, 5H), 4.69 (s, 2H), 6.81 (d, J=8.4 Hz, 2H), 7.11 (d, J=8.2 Hz, 2H), 7.3–7.6 (m, 5H).

Preparation 48

Ethyl 2-bromo-3-[4-[2-[N-(6-benzyloxy-2,5,7,8-tetramethylchroman-2-ylmethyl)-N-ethylamino]ethoxy]phenyl]propionate

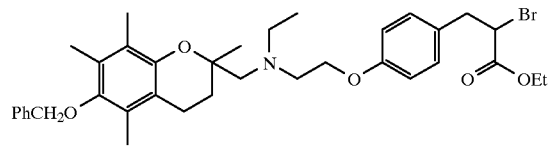

The title compound was prepared from 4-[2-[N-(6-benzyloxy-2,5,7,8-tetramethylchroman-2-ylmethyl)-N-ethylamino]ethoxy]aniline (4 g), obtained in preparation 41, by a similar procedure to that described in preparation 44.

$^1$H NMR (CDCl$_3$, 200 MHz): 1.08 (t, J=6.8 Hz, 3H), 1.15–1.40 (m, 6H), 1.60–1.80 (m, 1H), 1.90–2.05 (m, 1H), 2.06 (s, 3H), 2.17 (s, 3H), 2.20 (s, 3H), 2.55–2.90 (m, 6H), 3.0–3.25 (m, 3H), 3.30–3.50 (m, 1H), 4.0–4.25 (m, 4H), 4.25–4.40 (m, 1H), 4.69 (s, 2H), 6.80 (d, J=8.4 Hz, 2H), 7.10 (d, J=8.6 Hz, 2H), 7.30–7.60 (m, 5H).

Preparation 49

Ethyl 2-bromo-3-[4-[2-[N-(5-benzyloxy-2,3-dihydro-2,2,4,6,7-pentamethyl-1-benzofuran-3-ylmethyl)-N-methylamino]ethoxy]phenyl]propionate

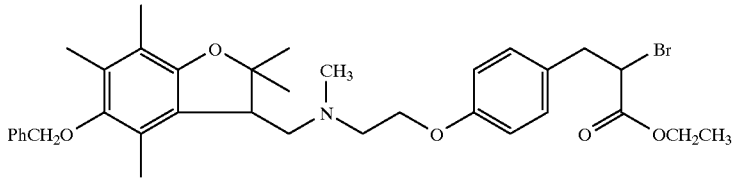

The title compound was prepared from 4-[2-[N-(5-benzyloxy-2,3-dihydro-2,2,4,6,7-pentamethyl-1-benzofuran-3-ylmethyl)-N-methylamino]ethoxy]aniline (4.3 g), obtained in preparation 42, by a similar procedure to that described in preparation 44.

$^1$H NMR (CDCl$_3$, 200 MHz): 1.28 (t, J=6.9 Hz, 3H), 1.38 (s, 3H), 1.63 (s, 3H), 2.11 (s, 3H), 2.23 (s, 3H), 2.28 (s, 3H), 2.41 (s, 3H), 2.72 (m, 2H), 2.91 (m, 2H), 3.10 (m, 1H), 3.22 (m, 1H), 3.40 (m, 1H), 4.08 (m, 2H), 4.18 (q, J=6.9 Hz, 2H), 4.36 (m, 1H), 4.72 (s, 2H), 6.82 (d, J=8.2 Hz, 2H), 7.14 (d, J=8.2 Hz, 2H), 7.48 (m, 5H).

EXAMPLE 1

5-[4-[2-[N-(6-Benzyloxy-2,5,7,8-tetramethylchroman-2-ylmethyl)-N-methylamino]ethoxy]phenyl methylene]thiazolidine-2,4-dione

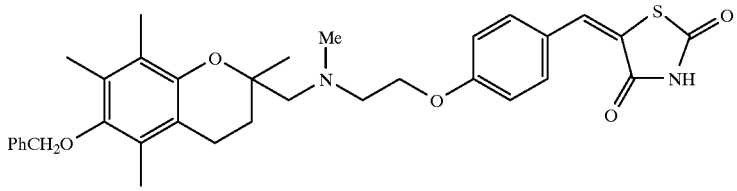

A solution of 4-[2-[N-(6-benzyloxy-2,5,7,8-tetramethylchroman-2-ylmethyl)-N-methylamino]ethoxy]benzaldehyde (12.8 g) obtained preparation 23 and 2,4-thiazolidinedione (3.2 g) in toluene (100 ml) containing piperidine (0.3 g) and benzoic acid (0.4 g) was heated at reflux for 2 h using a Dean Stark apparatus. The reaction mixture was cooled and filtered; the filtrate was washed with H$_2$O, dried (Na$_2$SO$_4$) and evaporated under reduced pressure. The crude product was chromatographed on silicagel using 2 to 10% (gradient elution) of methanol in benzene to afford 15.3 g of the title compound.

$^1$H NMR (CDCl$_3$, 200 MHz): δ1.25 (s, 3H), 1.70 (m, 1H), 2.0 (m, 1H), 2.07 (s, 3H), 2.18 (s, 3H), 2.2 (s, 3H), 2.52 (s, 3H), 2.65 (t, J=10.9 Hz, 2H), 2.7 (s, 2H), 3.05 (t, J=5.8 Hz, 2H), 4.15 (t, J=5.8 Hz, 2H), 4.7 (s, 2H), 6.95 (d, J=8.8 Hz, 2H), 7.4 (m, 7H), 7.75 (s, 1H).

EXAMPLE 2

5-[4-[2-[N-[2-(6-Benzyloxy-2,5,7,8-tetramethylchroman-2yl)ethyl]-N-methylamino]ethoxy]phenyl methylene]thiazolidine-2,4-dione

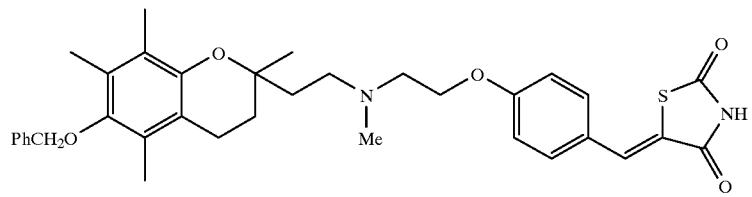

The title compound was prepared from 4-[2-[N-[2-(6-benzyloxy-2,5,7,8-tetramethylchroman-2-yl)ethyl]-N-methylamino]ethoxy]benzaldehyde, obtained in preparation 24, by a similar procedure to that described in example 1.

¹H NMR (CDCl₃, 200 MHz): δ1.3 (s, 3H), 1.85 (m, 4H), 2.05 (s, 3H), 2.15 (s, 3H), 2.22 (s, 3H), 2.45 (s, 3H), 2.65–3.0 (m, 6H), 4.15 (m, 2H), 4.7 (s, 2H), 6.95 (d, J=8.5 Hz, 2H), 7.3–7.55 (m, 7H), 7.6 (s, 1H).

EXAMPLE 3

5-[4-[2-[N-(6-Benzyloxy-2,5,7,8-tetramethylchroman-2-ylmethyl)amino]ethoxy] phenyl methylene]thiazolidine-2,4-dione

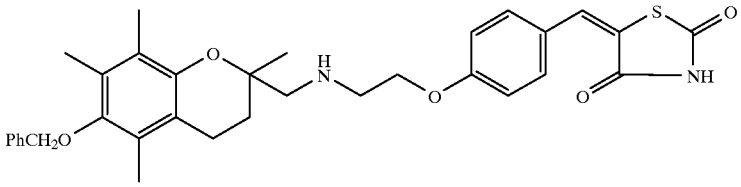

The title compound was prepared from 4-[2-[N-(6-benzyloxy-2,5,7,8-tetramethylchroman-2-ylmethyl)amino] ethoxy]benzaldehyde, obtained in preparation 25, by a similar procedure to that described in example 1.

¹H NMR (DMSO-d₆, 200 MHz): δ1.25 (s, 3H), 1.65–1.82 (m, 1H), 1.85–2.05 (m, 1H), 2.02 (s, 3H), 2.10 (s, 3H), 2.12 (s, 3H), 2.58 (m, 2H), 2.89 (s, 2H), 3.11 (m, 2H), 4.18 (m, 2H), 4.61 (s, 2H), 7.07 (d, J=8.8 Hz, 2H), 7.30–7.70 (m, 8H).

EXAMPLE 4

5-[4-[2-[N-(6-Benzyloxy-2,5,7,8-tetramethylchroman-2-ylmethyl)-N-ethylamino] ethoxy]phenyl methylene]thiazolidine-2,4-dione

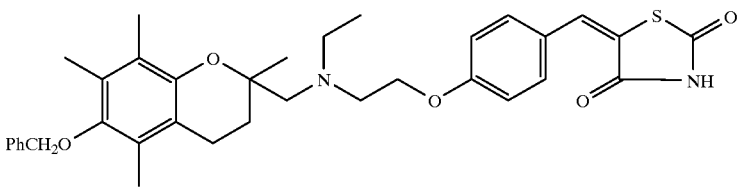

The title compound was prepared from 4-[2-[N-(6-benzyloxy-2,5,7,8-tetramethylchroman-2-ylmethyl)-N-ethylamino]ethoxy]benzaldehyde, obtained in preparation 26, by a similar procedure to that described in example 1.

¹H NMR (CDCl₃, 200 MHz): δ1.08 (m, 3H), 1.23 (s, 3H), 1.60–1.80 (m, 1H), 1.95–2.05 (m, 1H), 2.05 (s, 3H), 2.17 (s, 3H), 2.19 (s, 3H), 2.55–2.90 (m, 6H), 3.09 (m, 2H), 4.11 (m, 2H), 4.69 (s, 2H), 6.94 (d, J=8.2 Hz, 2H), 7.20–7.60 (m, 7H), 7.78 (s, 1H).

EXAMPLE 5

5-[4-[2-[N-(5-Benzyloxy-2,3-dihydro-2,2,4,6,7-pentamethyl-1-benzofuran-3-ylmethyl)-N-methylamino]ethoxy]phenyl methylene]thiazolidine-2,4-dione

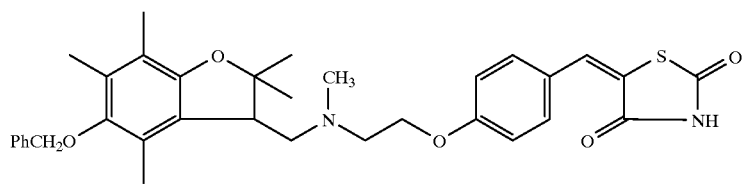

The title compound was prepared from 4-[2-[N-(5-benzyloxy-2,3-dihydro-2,2,4,6,7-pentamethyl-1-benzofuran-3-ylmethyl)-N-methylamino]ethoxy]benzaldehyde, obtained in preparation 27, by a similar procedure to that described in example 1.

¹H NMR (CDCl₃, 200 MHz): δ1.32 (s, 3H), 1.63 (s, 3H), 2.11 (s, 3H), 2.22 (s, 3H), 2.27 (s, 3H), 2.43 (s, 3H), 2.79 (m, 2H), 2.98 (m, 2H), 3.10 (m, 1H), 4.14 (m, 2H), 4.73 (s, 2H), 7.0 (d, J=8.3 Hz, 2H), 7.45 (m, 7H), 7.82 (s, 1H).

EXAMPLE 6

5-[6-[2-[N-(6-Benzyloxy-2,5,7,8-tetramethylchroman-2-ylmethyl)-N-methylamino]ethoxy-2-naphthyl methylene]thiazolidine-2,4-dione

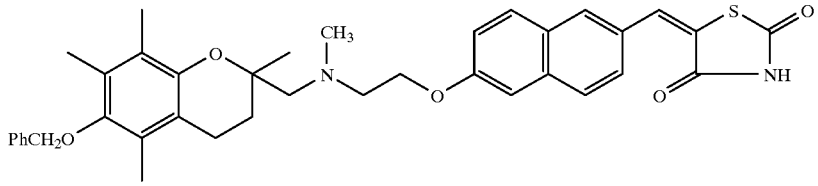

Sodium hydride (0.17 g, 50% dispersion in oil) was added in portions to a stirred solution of 5-[(6-hydroxy-2-naphthyl)methylene]-2,4-thiazolidinedione (1.3 g) in dry DMF (30 ml) under an atmosphere of nitrogen. After the effervescence has ceased, 2-(N-(6-benzyloxy-2,5,7,8-tetramethylchroman)-2-ylmethyl)-N-methylamino]ethyl chloride (1.9 g), obtained in preparation 13, was added and the reaction mixture was stirred at 80° C. for 3 hours. After cooling, the mixture was added to water (50 ml) and extracted with ethyl acetate (3×25 ml). The combined organic extract was washed with water, brine, dried (Na₂SO₄) and evaporated to dryness. Chromatography of the residue on silicagel with 30% EtOAc in petroleum ether afforded (1.2 g) the title compound.

¹H NMR (CDCl₃, 200 MHz) δ1.3 (s, 3H), 1.65–1.80 (m, 1H), 1.90–2.05 (m, 1H), 2.08 (s, 3H), 2.15 (s, 3H), 2.20 (s, 3H), 2.55 (s, 3H), 2.60–2.85 (m, 4H), 3.1 (m, 2H), 4.25 (m, 2H), 4.7 (s, 2H), 7.05–7.95 (m, 12H).

EXAMPLE 7

5-[4-[2-(N-Benzyl-N-methylamino)ethylthio]benzyl]thiazolidine-2,4-dione

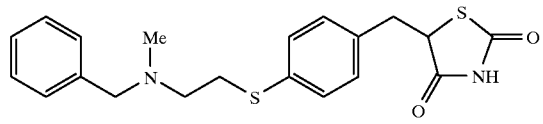

A mixture of ethyl 2-bromo-3-[4-[2-(N-benzyl-N-methylamino)ethylthio]phenyl]propionate (3 g), obtained in preparation 44, thiourea (520 mg), NaOAc (570 mg) and EtOH (21 ml) was stirred under reflux for 5 h and extracted with EtOAc, dried (Na₂SO₄) and concentrated to get 2-imino-5-[4-[2-(N-benzyl-N-methylamino)ethylthio]benzyl]-4-thiazolidinone which was used in the next step without further purification.

A mixture of the above crude compound, 2 N HCl (34 ml) and EtOH (34 ml) was stirred under reflux for 12 h. The reaction mixture was concentrated in vacuo. The residue was diluted with water, neutralised with saturated aqueous NaHCO₃ and extracted with ethyl acetate. The EtOAc extract was washed with brine, dried (Na₂SO₄) and concentrated in vacuo. The residue was chromatographed on silicagel with 40% EtOAc in petroleum ether as eluent to afford the title compound.

¹H NMR (CDCl₃, 200 MHz): δ2.26 (s, 3H), 2.66 (t, J=4.7 Hz, 2H), 3.1 (m, 3H), 3.45 (m, 1H), 3.55 (s, 2H), 4.52 (dd, J₁=9.5 Hz, J₂=3.6 Hz, 1H), 7.15 (d, J=8.2 Hz, 2H), 7.25 (d, J=8.2 Hz, 2H), 7.3 (s, 5H).

EXAMPLE 8

5-[4-[2-[N-(6-Benzyloxy-2,5,7,8-tetramethylchroman-2-ylmethyl)-N-methylamino]ethoxy]benzyl]thiazolidine-2,4-dione

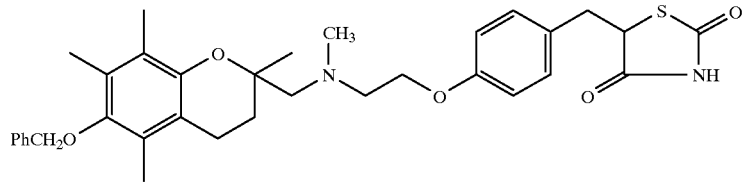

The title compound was prepared from ethyl 2-bromo-3-[4-[2-[N-(6-benzyloxy-2,5,7,8-tetramethylchroman-2- ylmethyl)-N-methylamino]ethoxy]phenyl]propionate, obtained in preparation 45, by a similar procedure to that described in example 7.

$^1$H NMR (CDCl$_3$, 200 MHz): δ1.26 (s, 3H), 1.60–1.80 (m, 1H), 1.90–2.05 (m, 1H), 2.09 (s, 3H), 2.17 (s, 3H), 2.22 (s, 3H), 2.52 (s, 3H), 2.60–2.80 (m, 4H), 2.90–3.20 (m, 3H), 3.35–3.50 (m, 1H), 4.1 (m, 2H), 4.40–4.55 (m, 1H), 4.69 (s, 2H), 6.82 (d, J=8.2 Hz, 2H), 7.12 (d, J=8.2 Hz, 2H), 7.30–7.60 (m, 5H).

EXAMPLE 9

5-[4-[2-[N-[2-(6-Benzyloxy-2,5,7,8-tetramethylchroman-2-yl)ethyl]-N-methylamino]ethoxy]benzyl]thiazolidine-2,4-dione

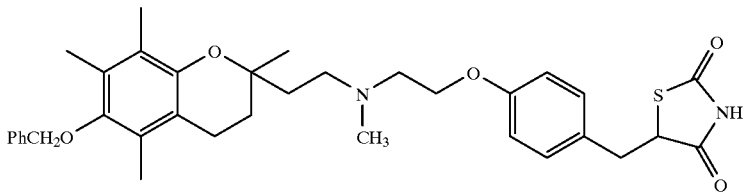

Method A

The title compound was prepared from Ethyl 2-bromo-3-[4-[2-[N-[2-(6-benzyloxy-2,5,7,8-tetramethylchroman-2-yl)ethyl]-N-methylamino]ethoxy]phenyl]propionate, obtained in preparation 47, by a similar procedure to that described in example 7.

Method B

The title compound was also prepared from 2-[N-[2-(6-benzyloxy-2,5,7,8-tetramethylchroman-2-yl)ethyl]-N-methylamino]ethyl chloride (2.3 g), obtained in preparation 16, and 5-[(4-hydroxyphenyl)methyl]thiazolidine-2,4-dione (1.2 g) by a similar procedure to that described in example 6.

$^1$H NMR (CDCl$_3$, 200 MHz): δ1.27 (s, 3H), 1.70–2.05 (m, 4H), 2.08 (s, 3H), 2.16 (s, 3H), 2.2 (s, 3H), 2.39 (s, 3H), 2.6 (t, J=6.4 Hz, 2H), 2.78 (t, J=7.9 Hz, 2H), 2.87 (t, J=5.1 Hz, 2H), 3.0–3.15 (m, 1H), 3.30–3.45 (m, 1H), 4.05 (m, 2H), 4.25–4.40 (dd, J$_1$=8.7 Hz, J$_2$=3.8 Hz, 1H), 4.68 (s, 2H), 6.76 (d, J=8.2 Hz, 2H), 7.11 (d, J=8.4 Hz, 2H), 7.3–7.55 (m, 5H).

EXAMPLE 10

5-[4-[2-[N-(6-Benzyloxy-2,5,7,8-tetramethylchroman-2-ylmethyl)-N-ethylamino]ethoxy]benzyl]thiazolidine-2,4-dione

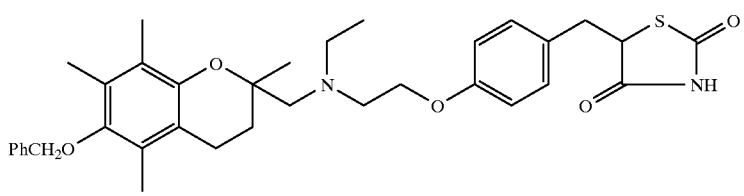

The title compound was prepared from ethyl 2-bromo-3-[4-[2-[N-(6-benzyloxy-2,5,7,8-tetramethylchroman-2-ylmethyl)-N-ethylamino]ethoxy]phenyl]propionate, obtained in preparation 48, by a similar procedure to that described in example 7.

$^1$H NMR (CDCl$_3$, 200 MHz): δ1.07 (t, J=6.6 Hz, 3H), 1.24 (s, 3H), 1.60–1.80 (m, 1H), 1.85–2.05 (m, 1H), 2.10 (s, 3H), 2.16 (s, 3H), 2.20 (s, 3H), 2.60–2.90 (m, 6H), 3.0–3.2 (m, 3H), 3.35–3.50 (m, 1H), 4.05 (m, 2H), 4.45–4.55 (m, 1H), 4.69 (s, 2H), 6.79 (d, J=8.2 Hz, 2H), 7.1 (d, J=8.4 Hz, 2H), 7.30–7.60 (m, 5H).

EXAMPLE 11

5-[4-[2-[N-(5-Benzyloxy-2,3-dihydro-2,2,4,6,7-pentamethyl-1-benzofuran-3-ylmethyl)-N-methylamino]ethoxy]benzyl]thiazolidine-2,4-dione

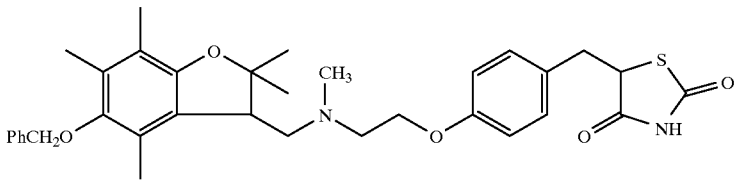

Method A

The title compound was prepared from ethyl 2-bromo-3-[4-[2-[N-(5-benzyloxy-2,3-dihydro-2,2,4,6,7-pentamethyl-1-benzofuran-3-ylmethyl)-N-methylamino]ethoxy]phenyl] propionate, obtained in preparation 49, by a similar procedure to that described in example 7.

Method B

The title compound was also prepared from 2-[N-(5-benzyloxy-2,3-dihydro-2,2,4,6,7-pentamethyl-1-benzofuran-3-ylmethyl)-N-methylamino]ethyl chloride (2 g), obtained in preparation 19, and 5-[(4-hydroxyphenyl)methyl]thiazolidine-2,4-dione (1.1 g) by a similar procedure to that described in example 6.

$^1$H NMR (CDCl$_3$, 200 MHz) δ1.33 (s, 3H), 1.58 (s, 3H), 2.08 (s, 3H), 2.18 (s, 3H), 2.23 (s, 3H), 2.36 (s, 3H), 2.73 (m, 2H), 2.91 (m, 2H), 3.08 (m, 2H), 3.42 (dd, J$_1$=14.1 Hz, J$_2$=3.7 Hz, 1H), 4.05 (t, J=5.6 Hz, 2H), 4.47 (dd, J$_1$=9.3 Hz, J$_2$=3.8 Hz, 1H), 4.70 (s, 2H), 6.82 (d, J=8.0 Hz, 2H), 7.12 (d, J=8.0 Hz, 2H), 7.45 (m, 5H).

To a solution of 12.5 g of the product obtained in example 1, in 120 ml of acetic acid was added 40 ml of concentrated hydrochloric acid. The resulting mixture was heated at 60° C. for 1 h. At the end of this time, the solvent was removed under reduced pressure and the residue was diluted with acetone. The resulting white solid was filtered and washed with excess of acetone. The solid was suspended in methanol and the pH was adjusted to 7 by the addition of triethylamine. The solvent was removed under reduced pressure and the resulting residue was dissolved in ethyl acetate and washed with water followed by brine. The organic layer was dried over anhydrous sodium sulphate and the solvent was removed by distillation under reduced pressure. The crude product was purified by column chromatography on silicagel using 2 to 10% (gradient elution) of methanol in chloroform to afford 9.8 g of the title compound.

$^1$H NMR (CDCl$_3$, 200 MHz): δ1.2 (s, 3H), 1.65 (m, 1H), 2.0 (m, 1H), 2.05 (s, 3H), 2.1 (s, 3H), 2.15 (s, 3H), 2.51 (s, 3H), 2.65 (m, 2H), 2.70 (s, 2H), 3.0 (t, J=5.6 Hz, 2H), 4.15 (t, J=5.8 Hz, 2H), 6.95 (d, J=8.8 Hz, 2H), 7.4 (d, J=8.8 Hz, 2H), 7.78 (s, 1H).

EXAMPLE 13
5-[4-[2-[N-[2-(6-Hydroxy-2,5,7,8-tetramethylchroman-2-yl)ethyl]-N-methylamino]ethoxy]phenyl methylene]thiazolidine-2,4-dione

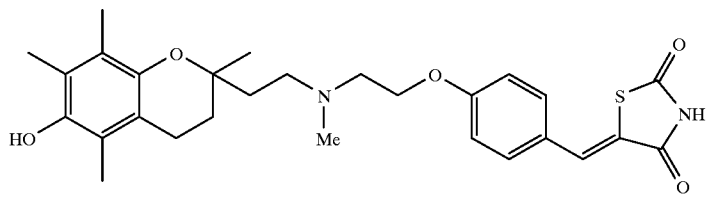

EXAMPLE 12

5-[4-[2-[N-(6-Hydroxy-2,5,7,8-tetramethylchroman-2-ylmethyl)-N-methylamino]ethoxy]phenyl methylene]thiazolidine-2,4-dione

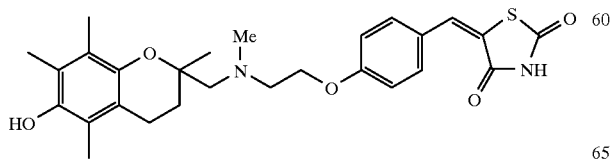

The title compound was prepared from the compound obtained in example 2, by a similar procedure to that described in example 12.

$^1$H NMR (CDCl$_3$, 200 MHz): δ1.3 (s, 3H), 1.85 (m, 4H), 2.1 (s, 6H), 2.15 (s, 3H), 2.45 (s, 3H), 2.65 (t, J=6.8 Hz, 2H), 2.8 (t, J=7.6 Hz, 2H), 2.9 (t, J=5.0 Hz, 2H), 4.15 (t, J=5.0 Hz, 2H), 6.95 (d, J=8.8 Hz, 2H), 7.35 (d, J=8.8 Hz, 2H), 7.55 (s, 1H).

EXAMPLE 14

5-[4-[2-[N-(6-Hydroxy-2,5,7,8-tetramethylchroman-2ylmethyl)amino]ethoxy]phenyl methylene]thiazolidine-2,4-dione

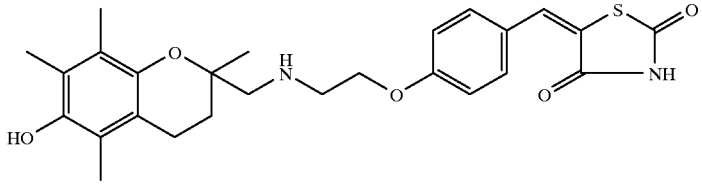

The title compound was prepared from 5-[4-[2-[N-(6-benzyloxy-2,5,7,8-tetramethylchroman-2-ylmethyl)amino]ethoxy]phenyl methylene]thiazolidine-2,4-dione, obtained in example 3, by an analogous procedure to that described in example 12.

$^1$H NMR (CDCl$_3$, 200 MHz): δ1.29 (s, 3H), 1.70–2.05 (m, 2H), 2.10 (s, 6H), 2.15 (s, 3H), 2.65 (t, J=6.6 Hz, 2H), 2.87 (s, 2H), 3.12 (t, J=4.6 Hz,2H), 4.14 (t, J=4.8 Hz, 2H), 6.94 (d. J=8.6 Hz, 2H), 7.38 (d, J=8.6 Hz, 2H), 7.85 (s, 1H).

EXAMPLE 15

5-[4-[2-[N-(6-Hydroxy-2,5,7,8-tetramethylchroman-2-ylmethyl)-N-ethylamino]ethoxy]phenyl methylene]thiazolidine-2,4-dione

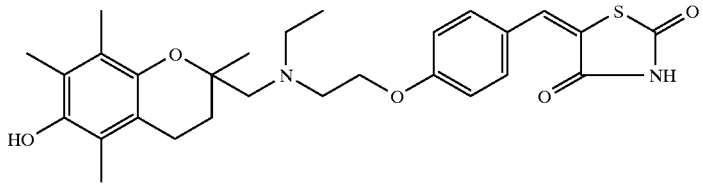

The title compound was prepared from 5-[4-[2-[N-(6-benzyloxy-2,5,7,8-tetramethylchroman-2-ylmethyl)-N-ethylamino]ethoxy]phenyl methylene]thiazolidine-2,4-dione, obtained in example 4, by an analogous procedure to that described in example 12.

$^1$H NMR (CDCl$_3$, 200 MHz): δ1.08 (t, J=7 Hz, 3H), 1.21 (s, 3H), 1.6–1.8 (m, 1H), 1.9–2.05 (m, 1H), 2.05 (s, 3H), 2.11 (s, 3H), 2.13 (s, 3H), 2.6–2.9 (m, 6H), 3.11 (t, J=5.8 Hz, 2H), 4.13 (t, J=5.8 Hz, 2H), 6.93 (d, J=8.6 Hz, 2H), 7.39 (d, J=8.6 Hz, 2H), 7.77 (s, 1H).

EXAMPLE 16

5-[4-[2-[N-(2,3-Dihydro-5-hydroxy-2,2,4,6,7-pentamethyl-1-benzofuran-3-ylmethyl)-N-methylamino]ethoxy]phenyl methylene]thiazolidine-2,4-dione

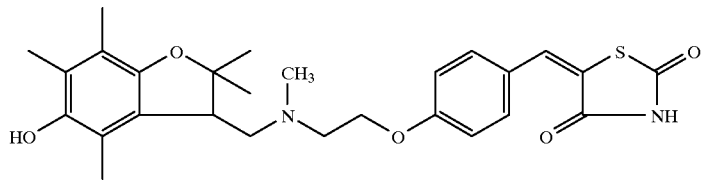

The title compound was prepared from 5-[4-[2-[N-(5-benzyloxy-2,3-dihydro-2,2,4,6,7-pentamethyl-1-benzofuran-3-ylmethyl)-N-methylamino]ethoxy]phenyl methylene]thiazolidine -2,4-dione, obtained in example 5, by an analogous procedure to that described in example 12.

¹H NMR (CDCl₃, 200 MHz): δ1.34 (s, 3H), 1.59 (s, 3H), 2.11 (s, 3H), 2.15 (s, 3H), 2.22 (s, 3H), 2.41 (s, 3H), 2.74 (m, 2H), 2.93 (m, 2H), 3.06 (m, 1H), 4.08 (m, 2H), 4.16 (bs, 1H), 6.98 (d, J=8.6 Hz, 2H), 7.48 (d, J=8.7 Hz, 2H), 7.83 (s, 1H).

EXAMPLE 17

5-[6-[2-[N-(6-Hydroxy-2,5,7,8-tetramethylchroman-2-ylmethyl)-N-methylamino]ethoxy]-2-naphthyl methylene]thiazolidine-2,4-dione

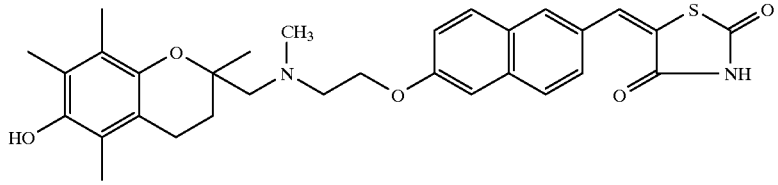

The title compound was prepared from 5-[6-[2-[N-(6-benzyloxy-2,5,7,8-tetramethylchroman-2-ylmethyl)-N-methylamino]ethoxy]-2-naphthyl methylene]thiazolidine-2,4-dione, obtained in example 6, by an analogous procedure to that described in example 12.

¹H NMR (CDCl₃, 200 MHz): δ1.25 (s, 3H), 1.60–1.80 (m, 1H), 1.90–2.05 (m, 1H), 2.07–2.20 (3s, 9H), 2.35–2.80 (m, 7H), 3.10 (m, 2H), 4.20 (m, 2H), 7.10–8.0 (m, 7H).

EXAMPLE 18

5-[4-[2-[N-Methyl-N-(5-methyl-2-phenyl-4oxazolyl) methylamino]ethoxy]phenyl methylene]thiazolidine-2,4-dione

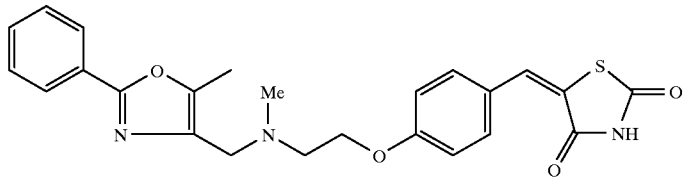

The title compound was prepared from 4-[2-[N-methyl-N-(5-methyl-2-phenyl-4-oxazolyl)methylamino]ethoxy] benzaldehyde, obtained in preparation 28, by a similar procedure to that described in example 1.

¹H NMR (CDCl₃, 200 MHz): δ2.4 (s, 3H), 2.5 (s, 3H), 3.05 (t, J=5.3 Hz, 2H), 3.75 (s, 2H), 4.25 (t, J=5.3 Hz, 2H), 6.9 (d, J=10.7 Hz, 2H), 7.35 (d, J=10.7 Hz, 2H), 7.45 (m, 3H), 7.55 (s, 1H), 8.0 (m, 2H).

EXAMPLE 19

5-[4-[2-[N-Methyl-N-(2-pyridylmethyl)amino] ethoxy]phenyl methylene]thiazolidine-2,4-dione

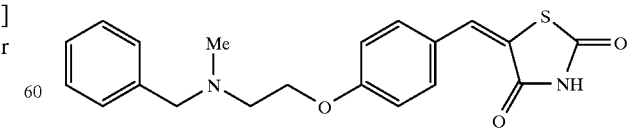

The title compound was prepared from 4-[2-[N-methyl-N-(2-pyridylmethyl)amino]ethoxy]benzaldehyde, obtained in preparation 29, by a similar procedure to that described in example 1.

¹H NMR (CDCl₃, 200 MHz): δ2.45 (s, 3H), 2.95 (m, 2H), 3.9 (s, 2H), 4.2 (m, 2H), 6.95 (d, J=7.4 Hz, 2H), 7.25 (m, 1H), 7.4 (d, J=7.4 Hz, 2H), 7.5 (d, J=7.3 Hz, 1H), 7.6 (s, 1H), 7.75 (t, J=7.4 Hz, 1H), 8.6 (d, J=3.7 Hz, 1H).

EXAMPLE 20

5-[4-[2-[N-Benzyl-N-methylamino]ethoxy]phenyl methylene]thiazolidine-2,4-dione

The title compound was prepared from 4-[2-[N-benzyl-N-methylamino]ethoxy]benzaldehyde, obtained in preparation 30, by a similar procedure to that described in example 1.

¹H NMR (CDCl₃, 200 MHz): δ2.4 (s, 3H), 2.9 (t, J=5.9 Hz, 2H), 3.7 (s, 2H), 4.15 (t, J=5.9 Hz, 2H), 6.95 (d, J=8.6 Hz, 2H), 7.2–7.6 (m, 7H), 7.65 (s, 1H).

EXAMPLE 21

5-[4-[2-[N-Methyl-N-(3-phenylpropyl)amino]ethoxy]phenyl methylene]thiazolidine-2,4-dione

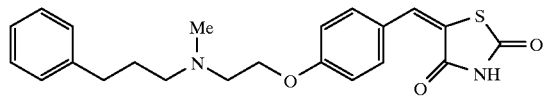

The title compound was prepared from 4-[2-[N-methyl-N-(3-phenylpropyl)amino]ethoxy]benzaldehyde, obtained in preparation 31, by a similar procedure to that described in example 1.

¹H NMR (CDCl₃+DMSO-d₆, 200 MHz) δ1.8–2.0 (m, 2H), 2.4 (s, 3H), 2.5–2.75 (m, 4H), 2.85 (t, J=5.4 Hz, 2H), 4.15 (t, J=5.6 Hz, 2H), 6.95 (d, J=8.8 Hz, 2H), 7.1–7.35 (m, 5H), 7.45 (d, J=8.6 Hz, 2H), 7.7 (s, 1H).

EXAMPLE 22

5-[4-[2-[N-Methyl-N-(3-phenylprop-2-enyl)amino]ethoxy]phenyl methylene]thiazolidine-2,4-dione

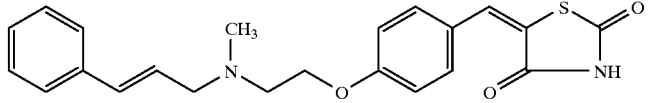

The title compound was prepared From 4-[2-[N-methyl-N-(3-phenylprop-2-enyl)amino]ethoxy]benzaldehyde, obtained in preparation 32, by a similar procedure to that described in example 1.

¹H NMR (CDCl₃, 200 MHz): δ2.53 (s, 3H), 3.0 (t, J=4.8 Hz, 2H), 3.43 (d, J=6.2 Hz, 2H), 4.22 (t, J=4.8 Hz, 2H), 6.35–6.50 (m, 1H), 6.61 (d, J=16.2 Hz, 1H), 6.93 (d, J=8.4 Hz, 2H), 7.20–7.60 (m, 8H).

EXAMPLE 23

5-[4-[2-[N-(6-Hydroxy-2,5,7,8-tetramethylchroman-2-ylmethyl)-N-methylamino]ethoxy]benzyl]thiazolidine-2,4-dione

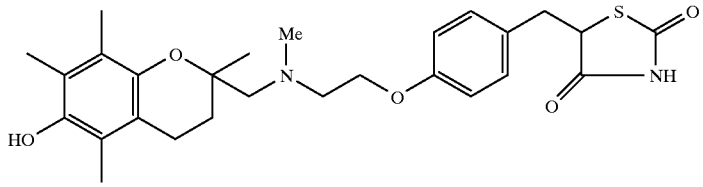

Method A

To a stirred suspension of the product obtained in the example 13, (4.25 g) in methanol (50 ml) at room temperature was added magnesium turnings (3.7 g) and the reaction mixture was stirred overnight at the same temperature. The reaction mixture was added to ice water (20 ml), the pH was adjusted to 6.5–7 using 10% aqueous hydrochloric acid and the solution was extracted with chloroform (3×75 ml). The combined organic extract was washed with H₂O, dried (CaCl₂) and the solvent was removed under reduced pressure. The residual mass was chromatographed on silicagel using 3% methanol in chloroform to give 3.9 g of the title compound.

Method B

The title compound was also prepared from 5-[4-[2-[N-(6-benzyloxy-2,5,7,8-tetramethylchroman-2-ylmethyl)-N-methylamino]ethoxy]benzyl]thiazolidine-2,4-dione, obtained in example 8, by a similar procedure to that described in example 12.

Method C

The title compound was also prepared from Ethyl 2-bromo-3-[4-[2-[N-(6-acetoxy-2,5,7,8-tetramethylchroman-2-ylmethyl)-N-methylamino]ethoxy]phenyl]propionate, obtained in preparation 46, by a similar procedure to that described in example 7.

¹H NMR (CDCl₃, 200 MHz): δ1.25 (s, 3H), 1.7 (m, 1H), 2.0 (m, 1H), 2.09 (s, 3H), 2.11 (s, 3H), 2.15 (s, 3H), 2.5 (s, 3H), 2.65 (bs, 4H), 2.97 (m, 2H), 3.1 (dd, J₁=14.1 Hz, J₂=9.4 Hz, 1H), 3.42 (dd, J₁=14.0 Hz, J₂=3.8 Hz, 1H), 4.05 (m, 2H), 4.5 (dd, J₁=8.9 Hz, J₂=4.0 Hz, 1H), 6.8 (d, J=9.35 Hz, 2H), 7.15 (d, J=9.55, 2H).

EXAMPLE 24

5-[4-[2-[N-[2-(6-Hydroxy-2,5,7,8-tetramethylchroman-2-yl)ethyl]-N-methylamino]ethoxy]benzyl]thiazolidine-2,4-dione

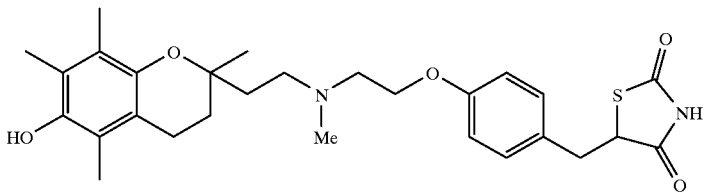

The title compound was prepared from 5-[4-[2-[N-[2-(6-benzyloxy-2,5,7,8-tetramethylchroman-2-yl)ethyl]-N-methylamino]ethoxy]benzyl]thiazolidine-2,4-dione obtained in example 9, by an analogous procedure to that described in example 12.

$^1$NMR (CDCl$_3$, 200 MHz): δ1.25 (s, 3H), 1.7–1.95 (m, 4H), 2.08 (s, 3H), 2.10 (s, 3H), 2.15 (s, 3H), 2.39 (s, 3H), 2.6 (t, J=6.6 Hz, 2H), 2.78 (t, J=7.9 Hz, 2H), 2.87 (t, J=5.4 Hz, 2H), 3.0–3.12 (m, 1H), 3.30–3.45 (m, 1H), 4.05 (m, 2H), 4.39–4.45 (dd, J$_1$=8.7 Hz, J$_2$=3.7 Hz, 1H), 6.76 (d, J=8.2 Hz, 2H), 7.11 (d, J=8.4 Hz, 2H).

EXAMPLE 25
5-[4-[2-(N-(6-Hydroxy-2,5,7,8-tetramethylchroman-2ylmethyl)-N-ethylamino]ethoxy]benzyl]thiazolidine-2,4-dione

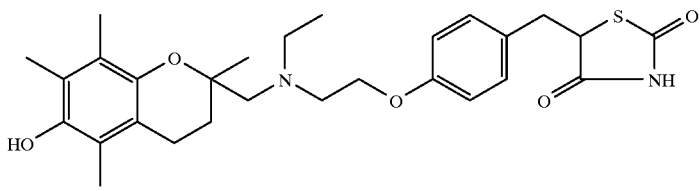

The title compound was prepared from 5-[4-[2-[N-(6-benzyloxy-2,5,7,8-tetramethylchroman-2-ylmethyl)-N-ethylamino)ethoxy]benzyl]thiazolidine-2,4-dione, obtained in example 10, by a similar procedure to that described in example 12.

$^1$H NMR (CDCl$_3$, 200 MHz): δ1.08 (t, J=7.0 Hz, 3H), 1.23 (s, 3H), 1.60–1.80 (m, 1H), 1.90–2.05 (m, 1H), 2.08 (s, 3H), 2.12 (s, 3H), 2.15 (s, 3H), 2.6–2.9 (m, 6H), 3.0–3.2 (m, 3H), 3.40–3.55 (m, 1H), 4.05 (m, 2H), 4.45–4.55 (m, 1H), 6.81 (d, J=8.4 Hz, 2H), 7.15 (d, J=8.6 Hz, 2H).

EXAMPLE 26
5-[4-[2-[N-(2,3-Dihydro-5-hydroxy-2,2,4,6,7-pentamethyl-1-benzofuran-3-ylmethyl)-N-methylamino]ethoxy]benzyl]thiazolidine-2,4-dione

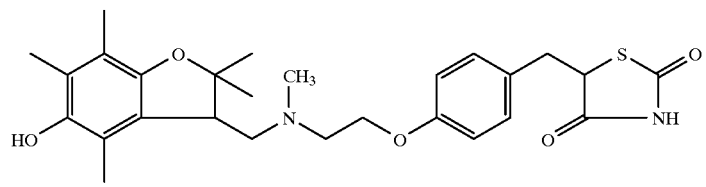

The title compound was prepared from 5-[4-[2-[N-(5-benzyloxy-2,3-dihydro-2,2,4,6,7-pentamethyl-1-benzofuran-3-ylmethyl)-N-methylamino]ethoxy]benzyl] thiazolidine-2,4-dione, obtained in example 11, by a similar procedure to that described in example 12.

$^1$H NMR (CDCl$_3$, 200 MHz): δ1.3 (s, 3H), 1.57 (s, 3H), 2.08 (s, 3H), 2.11 (s, 3H), 2.17 (s, 3H), 2.38 (s, 3H), 2.89 (m, 2H), 2.91 (m, 2H), 3.08 (m, 2H), 3.44 (dd, J$_1$=13.8 Hz, J$_2$=3.3 Hz, 1H), 4.0 (t, J=5.4 Hz, 2H), 4.49 (dd, J$_1$=9.4 Hz, J$_2$=3.8 Hz, 1H), 6.81 (d, J=8.3 Hz, 2H), 7.4 (d, J=8.3 Hz, 2H).

EXAMPLE 27

5-[4-[2-[N-Methyl-N-(5-methyl-2-phenyl-4-oxazolyl)methylamino]ethoxy]benzyl]thiazolidine-2,4-dione

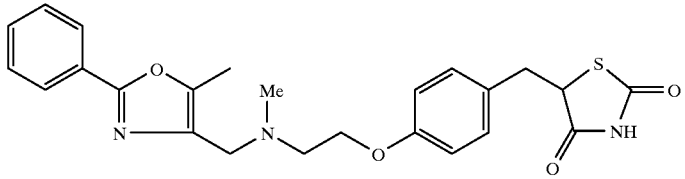

5-[4-[2-[N-methyl-N-(5-methyl-2-phenyl-4-oxazolyl)methylamino]ethoxy]phenyl methylene]thiazolidine-2,4-dione (2.5 g) obtained in example 18, was dissolved in dry 1,4-dioxane (100 ml) and was reduced with hydrogen (50 psig) in the presence of 10% palladium on charcoal (2.5 g) at ambient temperature until hydrogen uptake ceased. The solution was filtered through a bed of celite, the filter pad was washed exhaustively with dioxane and the combined filtrate was evaporated to dryness under reduced pressure to afford 2.5 g of the title compound after crystallisation from a mixture of benzene and petroleum ether.

$^1$H NMR (CDCl$_3$, 200 MHz): δ2.4 (s, 3H), 2.5 (s, 3H), 3.05 (m, 3H), 3.45 (dd, J$_1$=13.7 Hz, J$_2$=5.1 Hz, 1H), 3.7 (s, 2H), 4.2 (t, J=5.1 Hz, 2H), 4.45 (dd, J$_1$=10.3 Hz, J$_2$=3.4 Hz, 1H), 6.85 (d, J=6.8 Hz, 2H), 7.15 (d, J=6.8 Hz, 2H), 7.45 (m, 3H), 8.0 (m, 2H).

EXAMPLE 28

5-[4-[2-[N-Benzyl-N-methylamino]ethoxy]benzyl]thiazolidine-2,4-dione

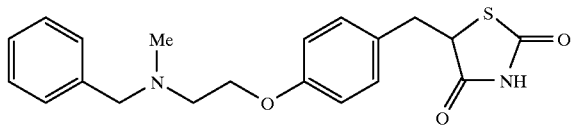

Method A

Sodium hydride (0.73 g, 50% dispersion in oil) was added in portions to a stirred solution of 5-[(4-hydroxyphenyl)methyl]thiazolidine-2,4-dione (1.4 g) in dry DMF (10 ml) under an atmosphere of nitrogen. After the effervescence has ceased, 2-[N-benzyl-N-methylamino]ethyl chloride (1 g), obtained in preparation 12, was added and the reaction mixture was stirred at room temperature overnight. After cooling, the mixture was added to water (50 ml) and extracted with ethyl acetate (3×50 ml). The combined organic extracts were washed with water, brine, dried (Na$_2$SO$_4$) and evaporated to dryness. Chromatography of the residue on silicagel with 2% methanol-chloroform gave 1.0 g of the title compound.

Method B

The title compound was also prepared from 5-[4-[2-[N-Benzyl-N-methylamino]ethoxy]phenyl methylene]thiazolidine-2,4-dione, obtained in example 20, by a similar procedure to that described in example 27.

$^1$H NMR (CDCl$_3$, 200 MHz): δ2.36 (s, 3H), 2.85 (t, J=5.8 Hz, 2H), 3.05–3.16 (dd, J$_1$=14.1 Hz, J$_2$=9.4 Hz, 1H), 3.39–3.50 (dd, J$_1$=14.1 Hz, J$_2$=4.0 Hz, 1H), 3.65 (s, 2H), 4.1 (t, J=5.8 Hz, 2H), 4.42–4.55 (dd, J$_1$=9.3 Hz, J$_2$=4.0 Hz, 1H), 6.85 (d, J=8.6 Hz, 2H), 7.15 (d, J=8.2 Hz, 2H), 7.35 (m, 5H).

EXAMPLE 29

5-[4-[2-[N-Methyl-N-(3-phenylpropyl)amino]ethoxy]benzyl]thiazolidine-2,4-dione

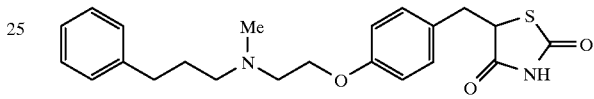

Method A

The title compound was prepared from 2-[N-methyl-N-(3-phenyl propyl)amino]ethyl chloride (1 g), obtained in preparation 21, and 5-[(4-hydroxyphenyl)methyl]thiazolidine-2,4-dione (1.36 g) by a similar procedure to that described in Method A of the example 28.

Method B

The title compound was also prepared from 5-[4-[2-[N-methyl-N-(3-phenylpropyl)amino]ethoxy]phenyl methylene]thiazolidine-2,4-dione, obtained in example 21, by a similar procedure to that described in Method A of the example 23.

$^1$H NMR (CDCl$_3$, 200 MHz): δ1.7–2.0 (m, 2H), 2.4 (s, 3H), 2.5–2.7 (m, 4H), 2.89 (t, J=5.4 Hz, 2H), 2.95–3.15 (dd, J$_1$=14.1 Hz, J$_2$=9.2 Hz, 1H), 3.3–3.35 (dd, J$_1$=14.1 Hz, J$_2$=3.8Hz, 1H), 4.05 (t, J=5.4 Hz, 2H), 4.35–4.45 (dd, J$_1$=9.1 Hz, J$_2$=3.8 Hz, 1H), 6.75 (d, J=8.4 Hz, 2H), 7.1–7.35 (m, 7H).

EXAMPLE 30

5-[4-[2-[N-Methyl-N-(3-phenylprop-2-enyl)amino]ethoxy]benzyl]thiazolidine-2,4-dione

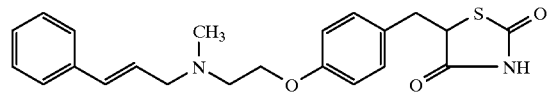

Method A

The title compound was prepared from 2-[N-methyl-N-(3-phenylprop-2-enyl)amino]ethyl chloride (1 g), obtained in preparation 22, and 5-[(4-hydroxyphenyl)methyl]thiazolidine-2,4-dione (1.38 g) by a similar procedure to that described in Method A of the example 28.

Method B

The title compound was also prepared from 5-[4-[2-[N-methyl-N-(3-phenylprop-2-enyl)amino]ethoxy]phenylmethylene]thiazolidine-2,4-dione, obtained in example 22, by a similar procedure to that described in Method A of the example 23.

$^1$H NMR (CDCl$_3$, 200 MHz): δ2.4 (s, 3H), 2.87 (t, J=5.6 Hz, 2H), 3.0–3.15 (dd, J$_1$=14.2 Hz, J$_2$=9.2 Hz, 1H), 3.3 (d, J=6.6 Hz, 2H), 3.35–3.50 (dd, J$_1$=14.1 Hz, J$_2$=3.2 Hz, 1H), 4.1 (t, J=5.6 Hz, 2H), 4.35–4.50 (dd, J$_1$=9.3 Hz, J$_2$=3.8 Hz, 1H), 6.2–6.4 (m, 1H), 6.55 (d, J=15.8 Hz, 1H), 6.85 (d, J=8.4 Hz, 2H), 7.10 (d, J=8.4 Hz, 2H), 7.2–7.5 (m, 5H).

The biological activity of the compound of the present invention on reducing blood sugar and blood lipid levels based on the ability of improving insulin resistance has been demonstrated by the following in vivo test.

Male C57BL/KsJ-db/db mice of 6 weeks age procured from the Jackson Laboratory, USA were used in the experiment. The mice were provided with standard pellets made by National Institute of Nutrition, Hyderabad, India and ad libitum water. The mice of 8 to 14 weeks age, having body weight 40 to 55 grams or more were used for testing.

The random blood sugar (RBS) values were measured by withdrawing blood (20 μl) through orbital sinus, using heparinised capillary, centrifuging the blood to obtain plasma and measuring the glucose level in the plasma by the glucose oxidase method using Stangen glucose-kit. The triglyceride levels in plasma were measured by glycerol 3 PO$_4$ oxidase/peroxidase enzyme method using Stangen kit. Four mice in a group having 300 mg/dl or more of the blood sugar level were used for the test.

The test compounds were suspended in 2.0% gum acacia and administered to test group at a dose of 200 mg/kg, through oral gavage daily for 10 days. The control group received the vehicle (Gum acacia 2% 10 ml/kg). The random blood sugar levels and triglyceride levels were measured at different time intervals before and after administration of test compounds. Troglitazone, (200 mg/kg daily dose) was used as a standard compound in the protocol.

The ability of reducing blood sugar level was determined as described below. The mean blood sugar values on zero day before administering the control vehicle (ZC) and treated group (TC) and the means of blood sugar values of the vehicle treated control on 3rd, 6th and 9th day and test compound treated group day control (DC) and day treated (DT).

The blood sugar lowering effect of test compound is calculated according to the following formula:

$$\text{Blood sugar lowering effect } (\%) = 1 - \frac{DT/TC}{DC/ZC} \times 100$$

The blood triglyceride (TG) lowering activity was calculated as percent reduction on the 9th day as compared to the control animal values.

| Compound | Maximum reduction in RBS level in a 9 days treatment (%) | Triglyceride lowering (%) |
|---|---|---|
| Example 12 | 43 | 70 |
| Troglitazone | 26 | Not Determined |

Toxicology: No toxicological effects were indicated for any of the mentioned compounds of invention in any of the above mentioned test.

The experimental results from the db/db mice suggest that the novel compounds of the present invention can also be a potential therapeutic utility for the treatment and/or prophylactic treatment of various cardiovascular diseases such as hypertension, hyperlipidaemia and other diseases; as it is known from the literature such diseases are interrelated to each other.

We claim:
1. A compound of formula (I),

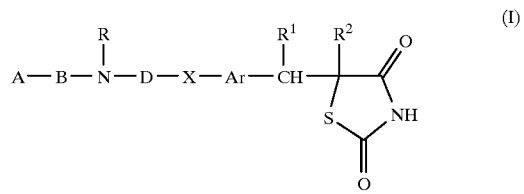

its tautomeric forms, its pharmaceutically acceptable salts, or its pharmaceutically acceptable solvates, where A represents a substituted or unsubstituted unsaturated aliphatic, alicyclic, aromatic, or heterocyclic group wherein when A is substituted, the substituents are selected from the group consisting of C$_1$–C$_{10}$ alkyl, C$_1$–C$_{10}$ alkoxy, aryl of single or fused, five or six membered rings, halogen, C$_7$–C$_{15}$ aralkyl, aryloxy, aralkoxy, amino, C$_1$–C$_8$ alkylamino, C$_1$–C$_8$ dialkylamino, amino-C$_1$–C$_8$ alkyl, hydroxy-C$_1$–C$_8$ alkyl, thio, thio-C$_1$–C$_8$ alkyl, halo-C$_1$–C$_8$ alkyl, carboxy, formyl, C$_2$–C$_{10}$ alkylcarbonyl, aryl carbonyl, aryl carbonyloxy, C$_2$–C$_{10}$ alkylcarbonyloxy, nitro and cyano; B represents a substituted or unsubstituted divalent alkenyl group of 2 to 10 carbon atoms or a substituted or unsubstituted divalent, alkylene group of 1 to 10 carbon atoms, wherein when the alkenyl or alkylene group is substituted, the substituents may be present in one or more of the divalent alkylene or alkenyl groups and the substituents are selected from C$_1$–C$_6$ alkylene, C$_2$–C$_6$ alkenyl, halogen atoms, C$_7$–C$_{15}$ aralkyl, amino, C$_1$–C$_8$ alkylamino, C$_1$–C$_8$ dialkylamino, amino-C$_1$–C$_8$ alkyl, hydroxy-C$_1$–C$_8$ alkyl, thio, thio-C$_1$–C$_8$ alkyl, halo-C$_1$–C$_8$ alkyl, carboxy, formyl, C$_2$–C$_{10}$ alkylcarbonyl, aryl carbonyl, nitro or cyano groups; D represents a substituted or unsubstituted divalent alkylene, alkenyl or alkynyl group; R represents hydrogen, substituted or unsubstituted alkylene, alkenyl or alkynyl, up to 10 carbon atoms, aralkyl, or alkoxycarbonyl or aryloxycarbonyl when A is not an aryl group; X represents CH$_2$, C=O, CH—OH, sulphur, oxygen, N-Y, where Y represents hydrogen, substituted or unsubstituted alkyl, aryl, aralkyl or acyl; Ar represents a divalent aromatic, single or fused ring system, with or without substituents, the ring may contain one or more hetero atoms selected from nitrogen, sulphur, or oxygen; and R$^1$ and R$^2$ each represents hydrogen or together represent a bond, either or both may be substituents or both together form a part of a ring.

2. A compound as claimed in claim 1 wherein, the unsaturated aliphatic group represented by A is a straight chain or branched chain with $C_1$–$C_{10}$ atoms or an alicyclic group with 1–3 rings which may or may not be substituted.

3. A compound as claimed in claim 1, wherein the aromatic and heterocyclic groups represented by A contain 1–3 rings, wherein in the heterocyclyl group there are up to 5 heteroatoms in the rings, selected from oxygen, sulphur or nitrogen.

4. A compound as claimed in claim 1, wherein the substituents of D are selected from $C_1$–$C_6$ alkylene, $C_2$–$C_6$ alkenyl, $C_2$–$C_6$ alkoxy, halogen atoms, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, aryl carbonyl, aryl carbonyloxy, $C_2$–$C_{10}$ alkylcarbonyloxy, hydroxy, nitro, or cyano.

5. A compound as claimed in claim 1, wherein Ar represents substituted or unsubstituted phenyl, naphthyl, pyridyl, furyl, benzofuryl, benzoxazolyl, or benzothiazolyl, the substituents on Ar are selected from $C_1$–$C_{10}$ alkyl, $C_1$–$C_{10}$ alkoxy, aryl of single of fused five or six membered rings halogen atoms, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy, hydroxy-$C_1$–$C_8$ alkyl, thio, thio-$C_1$–$C_8$ alkyl, carboxy, formyl, $C_2$–$C_{10}$ alkylcarbonyl, aryl carbonyl, aryl carbonyloxy, $C_2$–$C_{10}$ alkylcarbonyloxy, halo-$C_1$–$C_8$ alkyl, nitro or cyano.

6. A compound as claimed in claim 1, wherein $R^1$ and $R^2$ each independently represent a hydrogen atom, or together represent a bond, $R^1$ and $R^2$ either or both may represent a halogen atom, an alkyl group, or an alkoxy or a substituted or unsubstituted aryl group, or $R^1$ and $R^2$ together with the carbon atoms to which they are attached form a ring with 5 to 7 atoms.

7. A pharmaceutical composition for the treatment or prophylaxis of type II diabetes, hyperlipidaemia, hypertension, cardiovascular diseases, atherosclerosis or certain eating disorders which comprises a compound of the formula (I) as defined in claim 1, together with a pharmaceutically acceptable carrier, diluent, solvate or the like.

8. A pharmaceutical composition as claimed in claim 7, in the form of a tablet, capsule, powder, syrup, solution, suspension or the like.

9. A pharmaceutical composition as claimed in claim 7, further comprising flavourants, sweeteners or the like.

10. A compound as claimed in claim 1, wherein R represents hydrogen, substituted or unsubstituted, straight chain or branched $C_1$–$C_{10}$ alkylene, $C_2$–$C_{10}$ alkenyl, $C_2$–$C_{10}$ alkynyl, or aralkyl, wherein the aryl moiety may be substituted or unsubstituted, the substituents on the group represented by R are selected from $C_1$–$C_5$ alkyl, $C_1$–$C_4$ alkylcarbonyl, $C_1$–$C_6$ alkoxy, substituted or unsubstituted acyloxy, $C_1$–$C_4$ alkylcarbonyl, aryloxycarbonyl, hydroxy, amino, halogen or formyl group.

11. A compound according to claim 1, wherein the compound of formula (I) is selected from the group consisting of;

5-[4-[2-[N-(6-Benzyloxy-2,5,7,8-tetramethylchroman-2-ylmethyl)-N -methylamino]ethoxy]phenyl methylene] thiazolidine-2,4-dione;

5-[4-[2-[N-(6-Hydroxy-2,5,7,8-tetramethylchroman-2-ylmethyl) -N-methylamino]ethoxy]phenyl methylene] thiazolidine-2,4-dione;

5-[4-[2-[N-(6-Hydroxy-2,5,7,8-tetramethylchroman-2-ylmethyl) -N-methylamino]ethoxy]benzyl] thiazolidine-2,4-dione;

5-[4-[2-[N-Methyl-N-(5-methyl-2-phenyl4-oxazolyl) methylamino]ethoxy]phenyl methylene]thiazolidine-2, 4-dione;

5-[4-[2-[N-Methyl-N-(5-methyl-2-phenyl-4-oxazolyl) methylamino]ethoxy]benzyl]thiazolidine-2,4-dione;

5-[4-[2-[N-Methyl-N-(2-pyridyl)methylamino]ethoxy] phenyl methylene]thiazolidine-2,4-dione;

5-[4-[2-[N-Benzyl-N-methylamino]ethoxy]phenyl methylene]thiazolidine-2,4dione;

5-[4-[2-[N-Benzyl-N-methylamino]ethoxy]benzyl] thiazolidine-2,4dione;

5-[4-[2-[N-Methyl-N-(3-phenylpropyl)amino]ethoxy] phenyl methylene]thiazolidine -2,4-dione;

5-[4-[2-[N-Methyl-N-(3-phenylpropyl)amino]ethoxy] benzyl]thiazolidine-2,4-dione;

5-[4-[2-[N-Methyl-N-(3-phenyl-prop-2-enyl)amino] ethoxy]benzyl]thiazolidine-2,4-dione;

5-[4-[2-[N-Benzyl-N-methylamino)ethylthio]benzyl] thiazolidine-2,4-dione;

5-[4-[2-[N-(6-Benzyloxy-2,5,7,8-tetramethylchroman-2-ylethyl)-N-methylamino]ethoxy]phenyl methylene] thiazolidine-2,4-dione;

5-[4-[2-[N-(6-Hydroxy-2,5,7,8-tetramethylchroman-2-ylethyl)-N-methylamino]ethoxy]phenyl methylene] thiazolidine-2,4-dione;

5-[4-[2-[N-(6-Benzyloxy-2,5,7,8-tetramethylchroman-2-ylethyl)-N-methylamino]ethoxy]benzyl]thiazolidine-2, 4-dione; and 5-[4-[2-[N-(6-Hydroxy-2,5,7,8-tetramethylchroman-2-ylethyl)-N-methylamino]ethoxy]benzyl]thiazolidine-2, 4-dione.

12. A pharmaceutical composition for the treatment or prophylaxis of type II diabetes, hyperlipidaemia, hypertension, cardiovascular diseases, atherosclerosis or certain eating disorders which comprises a compound of the formula (I) as defined in claim 11, together with a pharmaceutically acceptable carrier, diluent, solvate or the like.

13. A pharmaceutical composition as claimed in claim 12, in the form of a tablet, capsule, powder, syrup, solution, suspension or the like.

14. A method for prophylactically treating or treating type II diabetes, hyperlipidaemia, hypertension, cardiovascular diseases, atherosclerosis or certain eating disorders which comprises administering an effective amount of a compound of the formula (I) as defined in claim 1, together with a pharmaceutically acceptable carrier, diluent, solvate or the like to a mammal in need thereof.

15. A method for prophylactically treating or treating type II diabetes, hyperlipidaemia, hypertension, cardiovascular diseases, atherosclerosis or certain eating disorders which comprises administering an effective amount of a compound of the formula (I) as defined in claim 11, together with a pharmaceutically acceptable carrier, diluent, solvate or the like to a mammal in need thereof.

16. A compound of the formula (I),

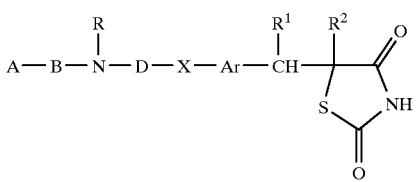

its tautomeric forms, its pharmaceutically acceptable salts, or its pharmaceutically acceptable solvates, where A represents a substituted or unsubstituted unsaturated aliphatic, alicyclic, aromatic, or heterocyclic group; B represents an unsubstituted divalent alkylene of 1 to 10 carbon atoms, or substituted or unsubstituted divalent alkenyl group of 2 to 10 carbon atoms; D represents a substituted or unsubstituted divalent alkylene, alkenyl or alkynyl group; R represents hydrogen, substituted or unsubstituted alkylene, alkenyl or alkynyl of up to 10 carbon atoms, aralkyl, or alkoxycarbonyl or aryloxycarbonyl when A is not an aryl group; X represents $CH_2$, $C=O$, CH—OH, sulphur, oxygen, N-Y, where Y represents hydrogen, substituted or unsubstituted alkyl, aryl, aralkyl or acyl; Ar represents a divalent aromatic, single or fused ring system, with or without substituents, the ring may contain one or more hetero atoms selected from nitrogen, sulphur, or oxygen; and $R^1$ and $R^2$ each represents hydrogen or together represent a bond, either or both may be substituents or both together form a part of a ring.

17. A compound as claimed in claim 16, wherein the unsaturated aliphatic group represented by A is a straight chain or branched chain with $C_1$–$C_{10}$ atoms or an alicyclic group with 1–3 rings which may or may not be substituted.

18. A compound as claimed in claim 16, wherein the aromatic and heterocyclic groups represented by A contain 1–3 rings, wherein in the heterocyclyl group there are up to 5 heteroatoms in the rings, selected from oxygen, sulphur or nitrogen.

19. A compound as claimed in claim 16, wherein the substituents in the group represented by A are selected from $C_1$–$C_{10}$ alkyl, $C_1$–$C_{10}$ alkoxy, aryl of single or fused, five or six membered rings, halogen, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy, hydroxy-$C_1$–$C_8$ alkyl, tho, thio-$C_1$–$C_8$ alkyl, halo-$C_1$–$C_8$ alkyl, carboxy, formyl, $C_2$–$C_{10}$ alkylcarbonyl, arylcarbonyl, arylcarbonyloxy, $C_2$–$C_{10}$ alkylcarbonyloxy, nitro or cyano.

20. A compound as claimed in claim 16, wherein the substituents of B are selected from $C_1$–$C_6$ alkylene, $C_2$–$C_6$ alkenyl, $C_2$–$C_6$ alkoxy, halogen atoms, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, aryl carbonyl, arylcarbonyloxy, $C_2$–$C_{10}$ alkylcarbonyloxy, nitro or cyano groups.

21. A compound as claimed in claim 16, wherein the substituents of D are selected from $C_1$–$C_6$ alkylene, $C_2$–$C_6$ alkenyl, $C_2$–$C_6$ alkoxy, halogen, atoms, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, aryl carbonyl, arylcarbonyloxy, $C_2$–$C_{10}$ alkylcarbonyloxy, hydroxy, nitro or cyano.

22. A compound as claimed in claim 16, wherein Ar represents substituted or unsubstituted phenyl, naphthyl, pyridyl, furyl, benzofuryl, benzoxazolyl, or benzothiazolyl, the substituents on Ar are selected from $C_1$–$C_{10}$ alkyl, $C_1$–$C_{10}$ alkoxy, aryl of single or fused five or six membered rings, halogen atoms, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy, hydroxy-$C_1$–$C_8$ alkyl, thio, thio-$C_1$–$C_8$ alkyl, carboxy, formyl, $C_2$–$C_{10}$ alkylcarbonyl, aryl carbonyl, aryl carbonyloxy, $C_2$–$C_{10}$ alkylcarbonyloxy, halo-$C_1$–$C_8$ alkyl, nitro or cyano.

23. A compound as claimed in claim 16, wherein $R^1$ and $R^2$ each independently represent a hydrogen atom, or together represent a bond, $R^1$ and $R^2$ either or both represent a halogen atom, an alkyl group, or an alkoxy or a substituted or unsubstituted aryl group, or $R^1$ and $R^2$ together with the carbon atoms to which they are attached, form a ring with 5 to 7 atoms.

24. A compound as claimed in claim 16, wherein R represents hydrogen, substituted or unsubstituted, straight chain or branched $C_1$–$C_{10}$ alkylene, $C_2$–$C_{10}$ alkenyl, $C_2$–$C_{10}$ alkynyl, or aralkyl, wherein the aryl moiety may be substituted or unsubstituted, the substituents on the group represented by R are selected from $C_1$–$C_{15}$ alkyl, $C_1$–$C_4$ alkylcarbonyl, $C_1$–$C_6$ alkoxy, substituted or unsubstituted acyloxy, $C_1$–$C_4$ alkylcarbonyl, aryloxycarbonyl, hydroxy, amino, halogen or formyl group.

25. A pharmaceutical composition for the treatment or prophylaxis of type II diabetes, hyperlipidaemia, hypertension, cardiovascular diseases, atherosclerosis or certain eating disorders which comprises a compound of the formula (I) as defined in claim 16, together with a pharmaceutically acceptable carrier, diluent or solvate.

26. A pharmaceutical composition as claimed in claim 25, in the form of a tablet, capsule, powder, syrup, solution, suspension or the like.

27. A pharmaceutical composition as claimed in claim 25, further comprising flavourants, sweeteners or the like.

28. A method for prophylactically treating or treating of type II diabetes, hyperlipidaemia, hypertension, cardiovascular diseases, atherosclerosis or certain eating disorders which comprises a compound of the formula (I) as defined in claim 16, together with a pharmaceutically acceptable carrier, diluent, solvate or the like.

29. A compound of the formula (I),

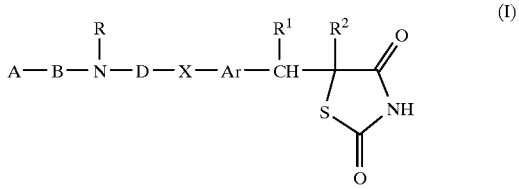

its tautomeric forms, its pharmaceutically acceptable salts, or its pharmaceutically acceptable solvates, where A represents a substituted or unsubstituted unsaturated aliphatic, alicyclic, aromatic, or heterocyclic group wherein when A is substituted, the substituents are selected from group consisting of $C_1$–$C_{10}$ alkyl, $C_1$–$C_{10}$ alkoxy, aryl of single or fused, five or six membered rings, halogen, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, arylcarbonyl, arylcarbonyloxy, $C_2$–$C_{10}$ alkylcarbonyloxy, nitro and cyano; B represents a substituted or unsubstituted divalent alkylene group of 1 to 10 carbon atoms, wherein when the alkylene group is substituted, the substituents may be present in one or more of the divalent alkylene groups and the substituents are selected from a $C_1$–$C_6$ alkylene, $C_2$–$C_6$ alkenyl, halogen atoms, $C_7$–$C_{15}$ aralkyl, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkyl carbonyl, aryl carbonyl, nitro or cyano groups; or B represents a substituted or unsubstituted divalent alkenyl group of 2 to 10 carbon atoms; wherein the substituents may be present in one or more of the divalent alkenyl groups, D represents a substituted or unsubstituted divalent alkylene, alkenyl or alkynyl group; R represents hydrogen, substituted or unsubstituted alkylene, alkenyl or alkynyl of up to 10 carbon atoms, aralkyl, or alkoxycarbonyl or aryloxycarbonyl when A is not an aryl group; X represents $CH_2$, C=O, CH—OH, sulphur, oxygen, N-Y, where Y represents hydrogen, substituted or unsubstituted alkyl, aryl, aralkyl or acyl; Ar represents a divalent aromatic, single or fused ring system, with or without substituents, the ring may contain one or more hetero atoms selected from nitrogen, sulphur, or oxygen; and $R^1$ and $R^2$ each represents hydrogen or together represent a bond, either or both may be substituents or both together form a part of a ring.

30. A compound as claimed in claim 29 wherein the unsaturated aliphatic group represented by A is a straight chain or branched chain with $C_1$–$C_{10}$ atoms or an alicyclic group with 1–3 rings which may or may not be substituted.

31. A compound as claimed in claim 29 wherein the aromatic and heterocyclic groups represented by A contain 1–3 rings, wherein the heterocyclyl group there are up to 5 heteroatoms in the rings, selected from oxygen, sulphur or nitrogen.

32. A compound as claimed in claim 29 wherein when B represents a substituted alkenyl group the substituents are selected from $C_1$–$C_6$ alkylene, $C_2$–$C_6$ alkenyl, $C_2$–$C_6$ alkoxy, halogen atoms, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ arylcarbonyl, aryl carbonyl, arylcarbonyloxy, $C_2$–$C_{10}$ alkylcarbonyloxy, nitro or cyano groups.

33. A compound as claimed in claim 29 wherein the substituents of D are selected from $C_1$–$C_6$ alkylene, $C_2$–$C_6$ alkenyl, $C_2$–$C_6$ alkoxy, halogen atoms, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, aryl carbonyl, arylcarbonyloxy, $C_2$–$C_{10}$ alkylcarbonyloxy, nitro or cyano.

34. A compound as claimed in claim 29 wherein Ar represents substituted or unsubstituted phenyl, naphthyl, pyridyl, furyl, benzofuryl, benzoxazolyl, or benzothiazolyl, the substituents on Ar are selected from $C_1$–$C_{10}$ alkyl, $C_1$–$C_{10}$ alkoxy, aryl of same or fused, five or six membered rings, halogen atoms, $C_1$–$C_{15}$ aralkyl, aryloxy, aralkoxy, amino, $C_1$–$C_8$ alkylamino, $C_1$–$C_8$ dialkylamino, amino $C_1$–$C_8$ alkyl, hydroxy, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, arylcarbonyl, arylcarbonyloxy, $C_2$–$C_{10}$ alkylcarbonyloxy, nitro or cyano.

35. A compound as claimed in claim 29 wherein $R^1$ and $R^2$ each independently represent a hydrogen atom, or together represent a hydrogen atom, or together represent a bond, $R^1$ and $R^2$ either or both represent a halogen atom, an alkyl group, or an alkoxy or a substitute or unsubstituted aryl group, or $R^1$ and $R^2$ together with the carbon atoms to which they are attached, form a ring with 5 to 7 atoms.

36. A pharmaceutical composition for the treatment or prophylaxis of type II diabetes, hyperlipidaemia, hypertension, cardiovascular diseases, atherosclerosis or certain eating disorders which comprises a compound of tie formula (I) as defined in claim 29 together with a pharmaceutically acceptable carrier, diluent, solvate or the like.

37. A pharmaceutical composition as claimed in claim 36 in the form of a tablet, capsule, powder, syrup, solution suspension of the like.

38. A pharmaceutical composition as claimed in claim 36 further comprising flavourants, sweeteners of the like.

39. A compound as claimed in claim 29 wherein R represents hydrogen, substituted or unsubstituted, straight chain or branched $C_1$–$C_{10}$ alkylene, $C_2$–$C_{10}$ alkenyl, $C_2$–$C_{10}$ alkynyl, or aralkyl, wherein the aryl moiety is substituted or unsubstituted, the substituents on the group represented by R are selected from $C_1$–$C_5$ alkyl, $C_1$–$C_4$ alkylcarbonyl, $C_1$–$C_6$ alkoxy, substituted or unsubstituted acyloxy, $C_1$–$C_4$ alkylcarbonyl, aryloxycarbonyl, hydroxy, amino, halogen or formyl carbonyl.

40. A method for prophylactically treating or treating type II diabetes, hyperlipidaemia, hypertension, cardiovascular diseases, atherosclerosis or certain eating disorders which comprises a compound of the formula (I) as defined in claim 29 together with a pharmaceutically acceptable carrier, diluent, solvate or the like.

41. A process for the preparation of thiazolidinedione derivatives of formula (I),

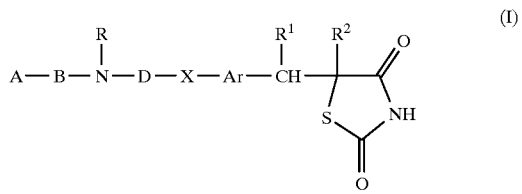

its tautomeric forms, its pharmaceutically acceptable salts, or its pharmaceutically acceptable solvates, where A represents a substituted or unsubstituted unsaturated aliphatic, alicyclic, aromatic, or heterocyclic group wherein when A is substituted, the substituents are selected from the group consisting of $C_1$–$C_{10}$ alkyl, $C_1$–$C_{10}$ alkoxy, aryl of single or fused, five or six membered rings, halogen, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, aryl carbonyl, aryl carbonyloxy, $C_2$–$C_{10}$ alkylcarbonyloxy, nitro and cyano; B represents a substituted or unsubstituted divalent alkenyl group of 2 to 10 carbon atoms or a substituted or unsubstituted divalent alkylene group of 1 to 10 carbon atoms, wherein when the alkenyl or alkylene group is substituted, the substituents may be present in one or more of the divalent alkylene or alkenyl groups and the substituents are selected from $C_1$–$C_6$ alkylene, $C_2$–$C_6$ alkenyl, halogen atoms, $C_7$–$C_{15}$ aralkyl, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, aryl carbonyl, nitro or cyano groups; D represents a substituted or unsubstituted divalent alkylene, alkenyl or alkynyl group; R represents hydrogen, substituted or unsubstituted alkylene, alkenyl or alkynyl group having up to 10 carbon atoms, aralkyl, or alkoxycarbonyl or aryloxycarbonyl when A is not an aryl group; X represents $CH_2$, C=O, CH—OH, sulphur, oxygen, N-Y, where Y represents hydrogen, substituted or unsubstituted alkyl, aryl, aralkyl or acyl; Ar represents a divalent aromatic, single or fused ring system, with or without substituents, the ring may contain one or more hetero atoms selected from nitrogen, sulphur, or oxygen; and $R^1$ and $R^2$ each represents hydrogen or together represent a bond, either or both may be substituents or both together form a part of a ring, said process comprises (a) reacting a compound of formula (V)

     (V)

where A and B as defined above, $L^1$ is a leaving group selected from OMs, OTf, Ots, Cl, Br, or I with the compound of formula (VI)

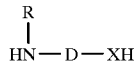     (VI)

where D and R are as defined above, X is selected from oxygen, sulphur or NH to obtain a compound of formula (VII)

     (VII)

where A, B, R, D and X are as defined above;

(b) reacting a compound of formula (VII) obtained in step (a) with a compound of formula (VIII)

$L^2$—Ar—CHO     (VIII)

where $L^2$ represents a halogen atom and Ar is as defined above, in an inert atmosphere to yield a compound of formula (IX)

     (IX)

where A, B, R, D, and Ar are as defined above, X is oxygen, sulfur or other hetero atom;

(c) reacting the compound of formula (IX) obtained in step (b) with 2,4-thiazolidinedione in the presence of a catalyst, to yield a compound of formula (X)

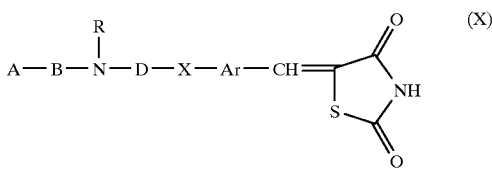     (X)

where A, B, R, D, Ar and X are as defined above, and removing water formed during the reaction; and (d) reducing the compound of formula (X) obtained in step (c) to obtain a compound of formula (I).

42. A process for converting the compound of formula (I) obtained in claim 41 into its pharmaceutically acceptable salts, its tautomeric forms or pharmaceutically acceptable solvates.

43. A process as claimed in claim 41 wherein the compound of formula (IX) of step (b) is prepared by reacting a compound of formula (XI)

     (XI)

wherein A, B, R, D, and $L^1$ are as defined in claim 32 with a compound of formula (XII)

HO—Ar—CHO     (XII)

where Ar is defined in claim 41.

44. A process for the preparation of thiazolidinedione derivatives of formula (I),

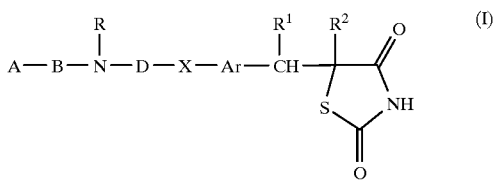     (I)

its tautomeric forms, its pharmaceutically acceptable salts, or its pharmaceutically acceptable solvates, where A represents a substituted or unsubstituted unsaturated aliphatic, alicyclic, aromatic, or heterocyclic group wherein when A is substituted, the substituents are selected from group consisting of $C_1$–$C_{10}$ alkyl, $C_1$–$C_{10}$ alkoxy, aryl of single or fused, five or six membered rings, halogen, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, arylcarbonyl, arylcarbonyloxy, $C_2$–$C_{10}$ alkylcarbonyloxy, nitro and cyano; B represents a substituted or unsubstituted divalent alkylene group of 1 to 10 carbon atoms, wherein when the alkylene group is substituted, the substituents may be present in one or more of the divalent alkylene groups and the substituents are selected from $C_1$–$C_6$ alkylene, $C_2$–$C_6$ alkenyl, halogen atoms, $C_7$–$C_{15}$ aralkyl, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkyl carbonyl, aryl carbonyl, nitro or cyano groups; or B represents a substituted or unsubstituted divalent alkenyl group of 2 to 10 carbon atoms; wherein the substituents may be present in one or more of the divalent alkenyl groups, D represents a substituted or unsubstituted divalent alkylene, alkenyl or alkynyl group; R represents hydrogen, substituted or unsubstituted alkylene, alkenyl or alkynyl having up to 10 carbon atoms, or aralkyl, or alkoxycarbonyl or aryloxycarbonyl when A is not an aryl group; X represents $CH_2$, C=O, CH—OH, sulphur, oxygen, N-Y, where Y represents hydrogen, substituted or unsubstituted alkyl, aryl, aralkyl or acyl; Ar represents a divalent aromatic, single or fused ring system, with or without substituents, the ring may contain one or more hetero atoms selected from nitrogen, sulphur, or oxygen; and $R^1$ and $R^2$ each represents hydrogen or together represent a bond, either or both may be substituents or both together form a part of a ring, said process comprises (a) reacting a compound of formula (V)

 (V)

where A and B as defined above, $L^1$ is a leaving group selected from OMs, OTf, Ots, Cl, Br, or I with the compound of formula (VI)

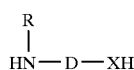 (VI)

where D and R are as defined above, X is selected from oxygen, sulphur or NH to obtain a compound of formula (VII)

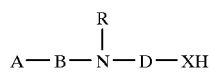 (VII)

where A, B, R, D and X are as defined above;

(b) reacting a compound of formula (VII) obtained in step (a) with a compound of formula (VIII)

$L^2$—Ar—CHO (VIII)

where $L^2$ represents a halogen atom and Ar is as defined above, in an inert atmosphere to yield a compound of formula (IX)

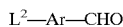 (IX)

where A, B, R, D, and Ar are as defined above, X is oxygen, sulfur or other hetero atom;

(c) reacting the compound of formula (IX) obtained in step (b) with 2,4-thiazolidinedione in the presence of a catalyst, to yield a compound of formula (X)

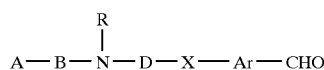 (X)

where A, B, R, D, Ar and X are as defined above, and removing water formed during the reaction; and (d) reducing the compound of formula (X) obtained in step (c) to obtain a compound of formula (I).

45. A process for converting the compound of formula (I) obtained in claim 44 into its pharmaceutically acceptable salts, its tautomeric forms or pharmaceutically acceptable solvates.

46. A process as claimed in claim 44 wherein the compound of formula (IX) of step (b) is prepared by reacting a compound of formula (XI)

 (XI)

wherein A, B, R, D, and $L^1$ are as defined in claim 44, with a compound of formula (XII)

HO—AR—CHO (XII)

wherein Ar is defined in claim 44.

47. A process for the preparation of thiazolidinedione derivatives of formula (I),

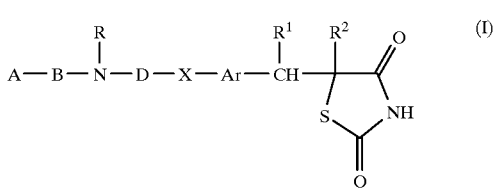 (I)

its tautomeric forms, its pharmaceutically acceptable salts, or its pharmaceutically acceptable solvates, where A represents a substituted or unsubstituted unsaturated aliphatic, alicyclic, aromatic, or heterocyclic group wherein when A is substituted, the substituents are selected from group consisting of $C_1$–$C_{10}$ alkyl, $C_1$–$C_{10}$ alkoxy, aryl of single or fused, five or six membered rings, halogen, $C_7$–$C_{15}$ aralkyl, aryloxy, aralkoxy, amino, $C_1$–$C_8$ alkylamino, $C_1$–$C_8$ dialkylamino, amino-$C_1$–$C_8$ alkyl, hydroxy-$C_1$–$C_8$ alkyl, thio, thio-$C_1$–$C_8$ alkyl, halo-$C_1$–$C_8$ alkyl, carboxy, formyl, $C_2$–$C_{10}$ alkylcarbonyl, arylcarbonyl, arylcarbonyloxy, $C_2$–$C_{10}$ alkylcarbonyloxy, nitro and cyano; B represents an unsubstituted divalent alkylene group of 1 to 10 carbon atoms, or a substituted or unsubstituted divalent alkenyl group of 2 to 10 carbon atoms; wherein the substituents may be present in one or more of the divalent alkenyl groups, D represents a substituted or unsubstituted divalent alkylene, alkenyl or alkynyl group; R represents hydrogen, substituted or unsubstituted alkylene, alkenyl or alkynyl, having up to 10 carbon atoms or aralkyl, or alkoxycarbonyl or aryloxycarbonyl when A is not an aryl group; X represents $CH_2$, C=O, CH—OH, sulphur, oxygen, N-Y, where Y represents hydrogen, substituted or unsubstituted alkyl, aryl, aralkyl or acyl; Ar represents a divalent aromatic, single or fused ring system, with or without substituents, the ring may contain one or more hetero atoms selected from nitrogen, sulphur, or oxygen; and $R^1$ and $R^2$ each represents hydrogen or together represent a bond, either or both may be substituents or both together form a part of a ring, said process comprises (a) reacting a compound of formula (V)

 (V)

where A and B as defined above, $L^1$ is a leaving group selected from OMs, OTf, Ots, Cl, Br, or I with the compound of formula (VI)

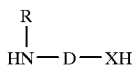 (VI)

where D and R are as defined above, X is selected from oxygen, sulphur or NH to obtain a compound of formula (VII)

 (VII)

where A, B, R, D and X are as defined above;

(b) reacting a compound of formula (VII) obtained in step (a) with a compound of formula (VIII)

 (VIII)

where $L^2$ represents a halogen atom and Ar is as defined above, in an inert atmosphere to yield a compound of formula (IX)

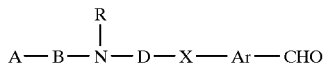 (IX)

where A, B, R, D and Ar are as defined above, X is oxygen, sulfur or other hetero atom;

(c) reacting the compound of formula (IX) obtained in step (b) with 2,4-thiazolidinedione in the presence of a catalyst, to yield a compound of formula (X)

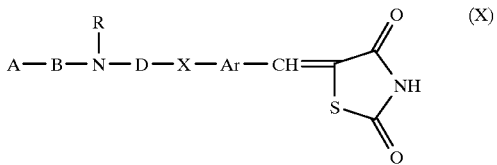 (X)

where A, B, R, D, Ar and X are as defined above, and removing water formed during the reaction; and (d) reducing the compound of formula (X) obtained in step (c) to obtain a compound of formula (I).

48. A process for converting the compound formula (I) obtained in claim 47 into its pharmaceutically acceptable salts, its tautomeric forms or pharmaceutically acceptable solvates.

49. A process as claimed in claim 47 wherein the compound of formula (IX) of step (b) is prepared by reacting a compound of formula (XI)

 (XI)

wherein A, B, R, D, and $L^1$ are as defined in claim 47, with a compound of formula (XII)

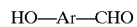 (XII)

wherein Ar is defined in claim 47.

* * * * *